US007323167B2

(12) United States Patent
Clark

(10) Patent No.: US 7,323,167 B2
(45) Date of Patent: *Jan. 29, 2008

(54) METHOD OF TREATMENT WITH MODIFIED ARGININE DEIMINASE

(75) Inventor: Mike A. Clark, Lexington, KY (US)

(73) Assignee: Polaris Group (TW)

( * ) Notice: Subject to any disclaimer, the term of this patent is extended or adjusted under 35 U.S.C. 154(b) by 404 days.

This patent is subject to a terminal disclaimer.

(21) Appl. No.: 10/757,843

(22) Filed: Jan. 15, 2004

(65) Prior Publication Data

US 2005/0129706 A1 Jun. 16, 2005

Related U.S. Application Data

(60) Division of application No. 09/723,546, filed on Nov. 28, 2000, now Pat. No. 6,737,259, which is a continuation-in-part of application No. 09/023,809, filed on Feb. 13, 1998, now Pat. No. 6,183,738.

(60) Provisional application No. 60/046,200, filed on May 12, 1997.

(51) Int. Cl.
 A61K 38/46 (2006.01)
 C12N 11/08 (2006.01)
 C12N 11/06 (2006.01)
 C12N 9/96 (2006.01)
 C12N 9/06 (2006.01)

(52) U.S. Cl. .................... 424/94.6; 435/180; 435/181; 435/188; 435/191

(58) Field of Classification Search ............... None
See application file for complete search history.

(56) References Cited

U.S. PATENT DOCUMENTS

| 4,179,337 | A | 12/1979 | Davis et al. ............ 435/181 |
| 4,609,546 | A | 9/1986 | Hiratani .................... 424/83 |
| 5,372,942 | A | 12/1994 | McGarrity et al. ........ 435/227 |
| 5,447,722 | A | 9/1995 | Lang et al. ............ 424/280.1 |
| 5,468,478 | A | 11/1995 | Saifer et al. ............ 424/78.27 |
| 5,474,928 | A | 12/1995 | Takaku et al. ............ 435/228 |
| 5,804,183 | A | 9/1998 | Filpula et al. ............ 424/94.6 |
| 5,916,793 | A | 6/1999 | Filpula et al. ............ 435/195 |
| 6,132,713 | A | 10/2000 | Fiipula et al. ............ 424/94.3 |

FOREIGN PATENT DOCUMENTS

| EP | 0 230 777 A1 | 8/1987 |
| EP | 0 372 752 A2 | 6/1990 |
| EP | 0 414 007 A2 | 2/1991 |
| EP | 0 442 724 A2 | 8/1991 |
| EP | 0 897 011 A2 | 2/1999 |
| JP | 53490 | 2/1990 |
| JP | 4 121 187 | 4/1992 |
| JP | 3 209 338 | 9/2001 |
| WO | WO 94/05332 | 3/1994 |
| WO | WO 96/34015 | 10/1996 |
| WO | WO 98/33519 | 8/1998 |
| WO | WO 98/51784 | 11/1998 |

OTHER PUBLICATIONS

Abuchowski, A. et al., "Effect of Covalent Attachment of Polyethylene Glycol on Immunogenicity and Circulating Life of Bovine Liver Catalase", *J. Biol. Chem.*, 1977, 252(11), 3582-3586.
Abuchowski, A., et al., "Treatment of L5178Y Tumor-Bearing BDF Mice with a Nonimmunogenic-Asparaginase", *Cancer Terat. Rep.*, 1979, 63(6), 1127-1132.
Gill, P. et al., "Inhibition of Cell Division in L5178Y Cells by Arginine-Degrading Mycoplasmas: The Frole of Arginine Deiminase", *Can. J. Microbiol.*, 1970, 16, 415-419.
Habeeb, A.F.S.A., "Determination of Free Amino Groups in Proteins by Trinitrobenezenesulfonic Acid", *Analyt. Biochem.*, 1966, 14, 328-336.
Hershfield, M.S. et al., "Treatment of Adenosine Deaminase", *New Engl. J. Medicine*, 1987, 316(10), 589-596.
Jeffe, N. et al., "Favorable Remission Induction Rate with Twice Weekely Doses of l-Asparaginase", *Cancer Res.*, 1973, 33(1), 1-4.
Jones, J.B., "The Effect of Arginine Deiminase on Murine Leukemic Lymphoblasts", *Ph.D. Dissertation, The University of Oklahoma*, 1981, 1-165.
Kamisaki, et al., "Increased Antitumor Activity of Escherichia Coli 1-Asparaginase by Modification with Monomethoxypolyethylene Glycol", *Gann*, 1982, 73-470-474.
Kamisaki, et al., "Reduction in Immunogenicity and Clearance Frate of *Escherichia Coli* 1-Asparaginase by Modification with Monomethoxypolyethylene Glycol", *J. Pharmacol. Exp. Ther.*, 1981, 216(2), 410-414.
Kidd, J.G. "Aspariginase and Cancer-Yesterday and Today", *Cancer Res.*, 1970, 33, 1-14.
Kondo, K. et al., "Cloning and Sequence Analysis of the Arginine Deiminase Gene from Mycoplasma Arginini", *Mol. Gen. Genet.*, 1990, 221, 81-86.
Misawa, S. et al., "High -Level Expression of Mycoplasma Arginine Deiminase in *Escherichia coli* and Its Efficient Renaturation as an Anti-Tumor Enzyme", *J. Biotechnology*, 1994, 36, 145-155.
Miyazaki, K. et al., "Potent Growth Inhibition of Human Tumor Cells in Culture by Aginine Deiminase Purified from a Culture Medium of a Mycoplasma-Infected Cell Line", *Cancer Res.*, 1990, 50,4522-4527.
Monfardini, C. et al., "A Branched Monomethoxypoly(Ethylene Glycol) for Protein Modification", *Bioconj. Chem.*, 1995, 6, 62-69.
Naio, M. et al., "Alteration of the Substrate Specificity of *Aspergillus oryzae* β-Galactosidase by Modification with Polyethylene Glycol", *J. Appl. Biochem.*, 1984, 6, 91-102.
Oginsky, "[92] Isolation and Determination of Arginine and Citrulline", *Meth. Enzymol.*, 1957, 3, 639-642.
Ohno, T. et al., "Cloning and Nucleotide Sequence of the Gene Encoding Arginine Deiminase of Mycoplasma Arginini", *Infect. Immun.*, 1990, 58, 3788-3795.
Park, Y.K. et al., "Pharmacology of *Escherichia coli*-L-Asparaginase Polyethylene Glycol Adduct", *Anticancer Res.*, 1981, 1, 373-376.

(Continued)

*Primary Examiner*—David M. Naff
(74) *Attorney, Agent, or Firm*—Woodcock Washburn LLP

(57) ABSTRACT

The present invention is directed to arginine deiminase modified with polyethylene glycol, to methods of treating cancer, and to methods of treating and/or inhibiting metastasis.

11 Claims, 10 Drawing Sheets

OTHER PUBLICATIONS

Pyatak, P.S. et al., "Preparation of a Polyethylene Glycol: Superoxide Dismutase Adduct and an Examination of its Blood Circulating Life and Anti-Inflammatory Activity", *Res. Commun. Chem. Path. Pharmacol.*, 1980, 29(1), 113-127.

Sayers, J.R. et al., "Rapid High-Efficiency Site Directed Mutagenesis by the Phosphorothioate Approach", *Biotechniques*, 1992, 13(4), 592-596.

Stocks, S.J. et al., "A Flurometric Assay of the Degree of Modification of Protein Primary Armines with Polyethylene Glycol", *Analyt. Biochem.*, 1986, 154, 232-234.

Su, T. et al., "Cloning of cDNA for Argininosuccinate Synthetase mRNA and Study of Enzyme Overproduction in a Human Cell Line", *J. Biol. Chem.*, 1981, 256(22), 11826-11831.

Sugimura, K. et al., "High Sensitivity of Human Melanoma Cell Lines to the Growth Inhibitory Activity of Mycoplasmal Arginine Deiminase in Vitro", *Melanoma Res.*, 1992, 2, 191-196.

Sugimura, K. et al., "Identification and Purification of Arginine Deiminase that Originated from Mycoplasma Arginini", *Infect Immun.*, 1990, 58*8, 2510-2515.

Takaku, H. et al., "Anti-tumor Activity of Arginine Deiminase from Mycoplasma Arginini and its Growth-Inhibitory Mechanism", *Int. J. Cancer*, 1995, 86, 840-846.

Takaku, H. et al., "Chemical Modification by Polyethylene Glycol of the Anti-Tumor Enzyme Arginine Deiminase from Mycoplasma Arginini", *Jpn. J. Cancer Res.*, 1993, 84, 1195-1200.

Takaku, H. et al., "In Vivo Anti-Tumor Activity of Arginine Deiminase Purified From Mycoplasma Arginini", *Int. J. Cancer*, 1992, 51, 244-249.

Teske, E. et al., "Polyethylene Glycol-L-Aspariginase Versus Native L-Asparaginase in Canine Non-Hodgkin's Lymphoma", *Eur. J. Cancer*, 1990, 26(8), 891-895.

Zalipsky, et al., "Use of Functionalized Poly(Ethylene Glycol)s for Modification of Polypeptides", *Polyethylene Glycol Chem., Biotechnical and Biomedical Applns.*, 1992, 21, 347-370.

Misawa, S. et al., "High-Level Expression of *Mycoplasma* Arginine Deiminase in *Escherichia coli* and its Efficient Renaturation as an Anti-Tumor Enzyme", *J. Biotechnology*, 1994, 36, 145-155.

van Wagtendonk, et al., "Nitrogen metabolism in protozoa", *Comparative Biochemistry of Nitrogen Metabolism (J.W. Campbell ed.)*, 1970, 1-56.

Chang, et al. "Arginase modulates nitric oxide production in activated macrophages", *Am. J. Physiol: Heart and Circul. Physiol.*, 1998, 274, H342-H348.

McDonald, et al., "A Caveolar complex between the cationic amino acid transporter 1 and endothelial nitric-oxide synthase may explain the Arginine paradox", *J. Biol. Chem.*, 1997, 272, 31213-31216.

Deckers, P.J, et al. "The effect of tumor size on concomitant tumor immunity", *Cancer Res.*, 1973, 33(1), 33-39.

Fenske, J.D., et al., "Role of arginine deiminase in growth of *Mycoplasma hominus*", *J. Bacteriol.*, 1976, 126, 501-510.

Lang, K. et al., "Catalysis of protein folding by prolyl isomerase", *Nature*, 1987, 329, 268-270.

Craig, S. et al., "Single amino acid mutations block a late step in the folding og B-Lactamase from *Staphylococcus aureus*", *J. Mol. Biol.*, 1985, 185, 681-687.

Joppich, et al., "Peptides flanked by two polymer chains, 1-synthesis of Glycl-L-tryptophylglycine substituted by poly(ethylene oxide) at both the carboxy and the amino end groups", *Macromol. Chem.*, 1979, 180, 1381-1385.

Harasawa, R. et al., "Nucleotide Sequence of the Arginine Deiminase Gene of *Mycoplasma hominis*," *Microbiol. Immunol.*, 1992, 36(6), 661-665.

Takaku, H. et al., "Anti-tumor Activity of Arginine Deiminase from *Mycoplasma arginini* and Its Growth-inhibitory Mechanism," *Jpn. J. Cancer Res.*, Sep. 1995, 86(9), 840-846.

Fraser, C. et al., "*Borrelia burgdorferi* (section 69 of 70) of the complete genome", Dec. 16, 1997, Database Accession No. AE001183, XP 002211866.

Knodler, Leigh A. et al., "Cloning and Expression of a Prokaryotic Enzyme, Arginine Deiminase., from a Primitive Eukaryote *Giardia intestinalis*", *Journal of Biological Chemistry*, Feb. 20, 1998, 273(8), 4470-4477, XP-002211868.

Takaku, et al., *Jpn J. Cancer Res.*, 1993, 84, 1195-200.

Poyart, et al., *International Journal of Systematic and Evolutionary Microbiology*, 2002, 52, 1247-1255.

Tettelin, et al., *Science*, 2001, 293, 498-506.

Degnan, et al., *Infection and Immunity*, 1998, 66(7), 3050-3058.

Clark, R., et al., "Long-Acting Growth Hormones Produced by Conjugation with Polyethylene Glycol", *journal of Biological Chemistry*, 1996, 271, 21969-21977, XP-002216386.

Gaertner, H.F. et al., "Site-Specific Attachment of Functionalized Poly(Ethylene Glycol) to the Amino Terminus of Proteins", *Bioconjugate Chem.*, 1996, 7, 38-44, XP-000791225.

Kita, Y. et al., "Characterization of a Polyethylene Glycol Conjugate of Recombinant Human Interferon-y", *Drug Design and Delivery*, 1990, 6, 157-167.

Rigneault, H. et al., "Extraction of Light from Sources Located Inside Waveguide Grating Structures", *Optice Letters*, 1999, 24(3), 148-150, XP-000803121.

Molnar, S. et al., "Pharmacology of a Peg-Conjugated Arginine Deiminase", *Faseb Journal*,1993, 7, p. A391, XP009002632.

The alignment was done on 3 Protein sequences.
Character to show that a position in the alignment is perfectly conserved: '*'
Character to show that a position is well conserved: '.'

Alignment
```
ADIPROT    MSVFDSKFKGIHVYSEIGELESVLVHEPGREIDYITPARLDELLFSAILE    50
ARTADIPRO  MSVFDSKFKGIHVYSEIGELESVLVHEPGREIDYITPARLDELLFSAILE    50
HOMADIPRO  MSVFDSKFNGIHVYSEIGELETVLVHEPGREIDYITPARLDELLFSAILE    50
           ******** ******************.**********************

ADIPROT    SHDARKEHKQFVAELKANDINVVELIDLVAETYDLASQEAKDKLIEEFLE    100
ARTADIPRO  SHDARKEQSQFVAILKANDINVVETIDLVAETYDLASQEAKDRLIEEFLE    100
HOMADIPRO  SHDARKEHQSFVKIMKDRGINVVELTDLVAETYDLASKAAKEEFIETFLE    100
           *******. ** ...***** .**********..**..**.***

ADIPROT    DSEPVLSEEHKVVVRNFLKAKKTSRKLVEIMMAGITKYDLGIEADHELIV    150
ARTADIPRO  DSEPVLSEAHKKVVRNFLKAKKTSRKLVELMMAGITKYDLGVEADHELIV    150
HOMADIPRO  ETVPVLTEANKKAVRAFLLSKPT-HEMVEFMMSGITKYELGVESENELIV    149
           .. ***.*.* .**.** .* *   ..**.**.*****.** *...****

ADIPROT    DPMPNLYFTRDPFASVGNGVTIHYMRYKVRQRETLFSRFVFSNHPKLINT    200
ARTADIPRO  DPMPNLYFTRDPFASVGNGVTIHFMRYKVRRRETLFSRFVFRNHPKLVNT    200
HOMADIPRO  DPMPNLYFTRDPFASVGNGVTIHFMRYIVRRRETLFARFVFRNHPKLVKT    199
           *********************** ***.*** ****** ****.*****..

ADIPROT    PWYYDPSLKLSIEGGDVFIYNNDTLVVGVSERTDLQTVTLLAKNIVANKE    250
ARTADIPRO  PWYYDPAMKLSIEGGDVFIYNNDTLVVGVSERTDLDTVTLLAKNLVANKE    250
HOMADIPRO  PWYYDPAMKMPIEGGDVFIYNNETLVVGVSERTDLDTITLLAKNIKANKE    249
           ******..*.. .************.*********. *.*****..****

ADIPROT    CEFKRIVAINVPKWTNLMHLDTWLTMLDKDKFLYSPIANDVFKFWDYDLV    300
ARTADIPRO  CEFKRIVAINVPKWTNLMHLDTWLTMLDKNKFLYSPIANDVFKFWDYDLV    300
HOMADIPRO  VEFKRIVAINVPKWTNLMHLDTWLTMLDKNKFLYSPIANDVFKFWDYDLV    299
            ***************************.*********************

ADIPROT    NGGAEPQPVENGLPLEGLLQSIINKKPVLIPIAGEGASQMEIERETHFDG    350
ARTADIPRO  NGGAEPQPVENGLPLEKLLQSIINKKPVLIPIAGEGASQMEIERETHFDG    350
HOMADIPRO  NGGAEPQPQLNGLPLDKLLASIINKEPVLIPIGGAGATEMEIARETNFDG    349
           ********  ***** ** .*****.******.** ** *** *** ***

ADIPROT    TNYLAIRPGVVIGYSRNEKTNAALEAAGIKVLPFHGNQLSLGMGNARCMS    400
ARTADIPRO  TNYIAIRPGVVIGYSRNEKTNAALKAAGIKVLPFHGNQLSLGMGNARCMS    400
HOMADIPRO  TNYLAIKPGLVIGYDRNEKTNAALKAAGITVLPFHGNQLSLGMGNARCMS    399
           ***.**.** ****.********.****.********************

ADIPROT    MPLSRKDVKW    410
ARTADIPRO  MPLSRKDVKW    410
HOMADIPRO  MPLSRKDVKW    409
           **********
```

| | |
|---|---|
| ADIPROT | = *Mycoplasma arginini* |
| ARTADIPRO | = *Mycoplasma arthritides* |
| HOMADIPRO | = *Mycoplasma hominus* |

FIG. 1

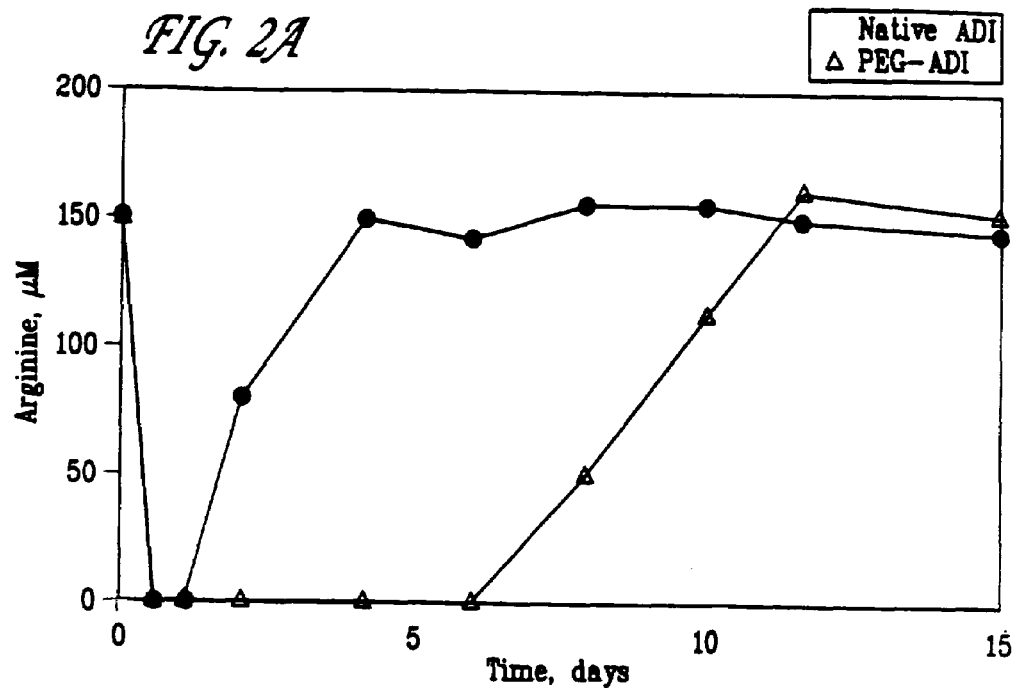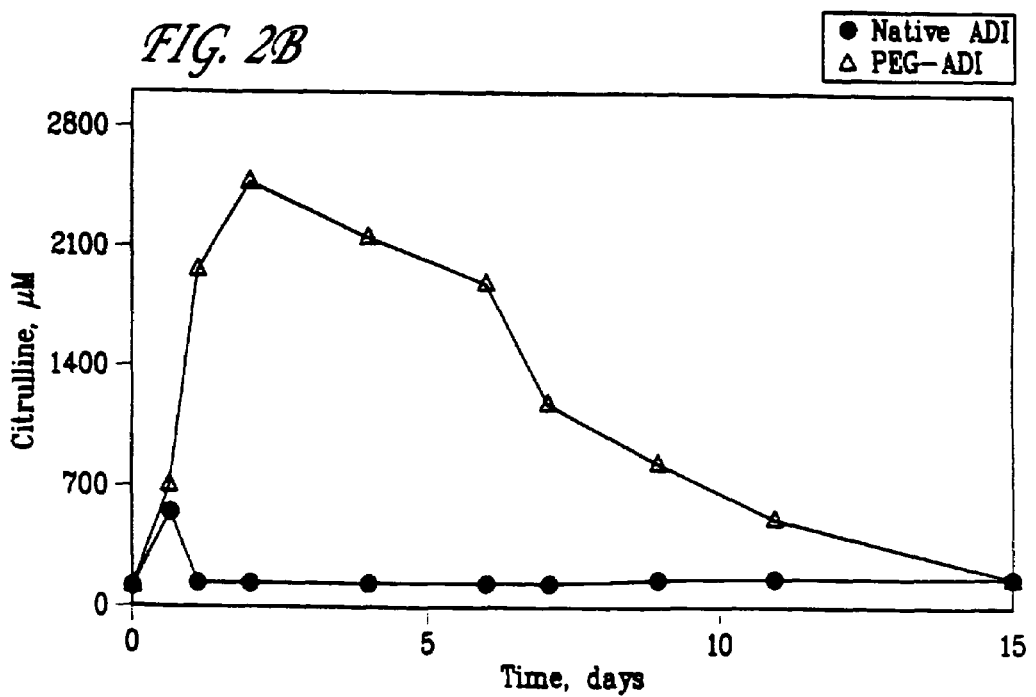

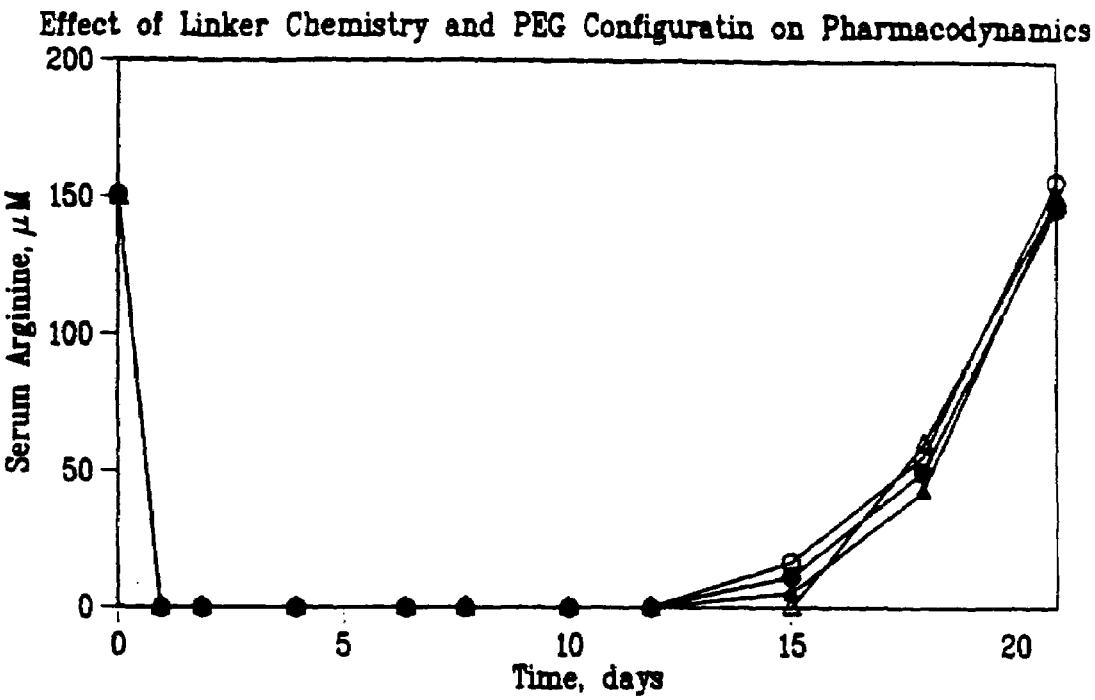
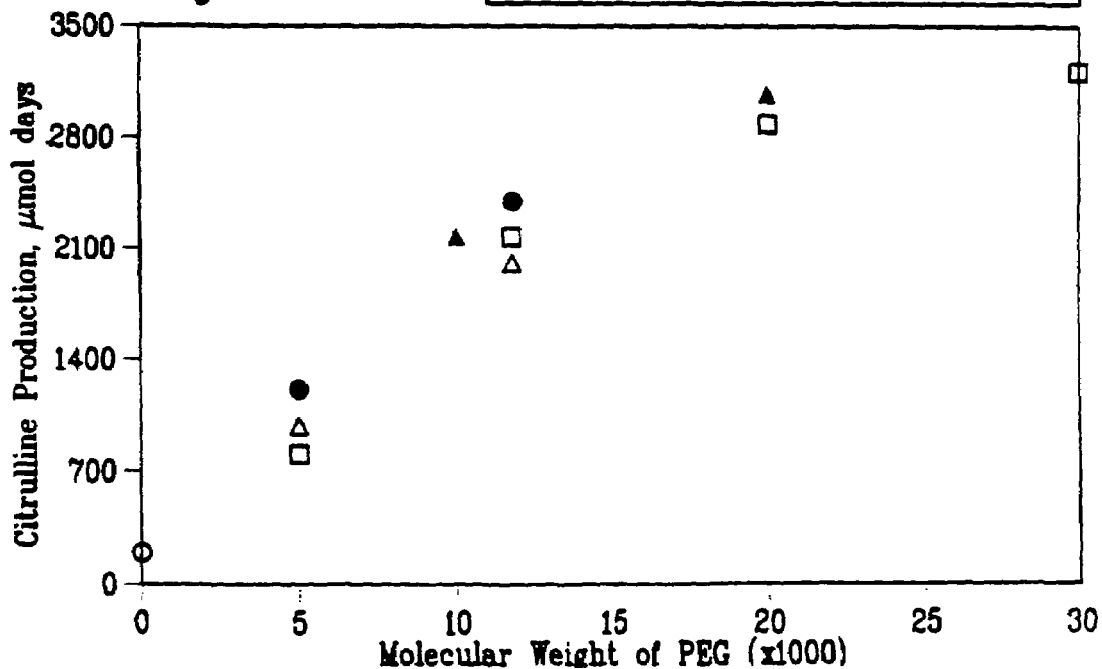

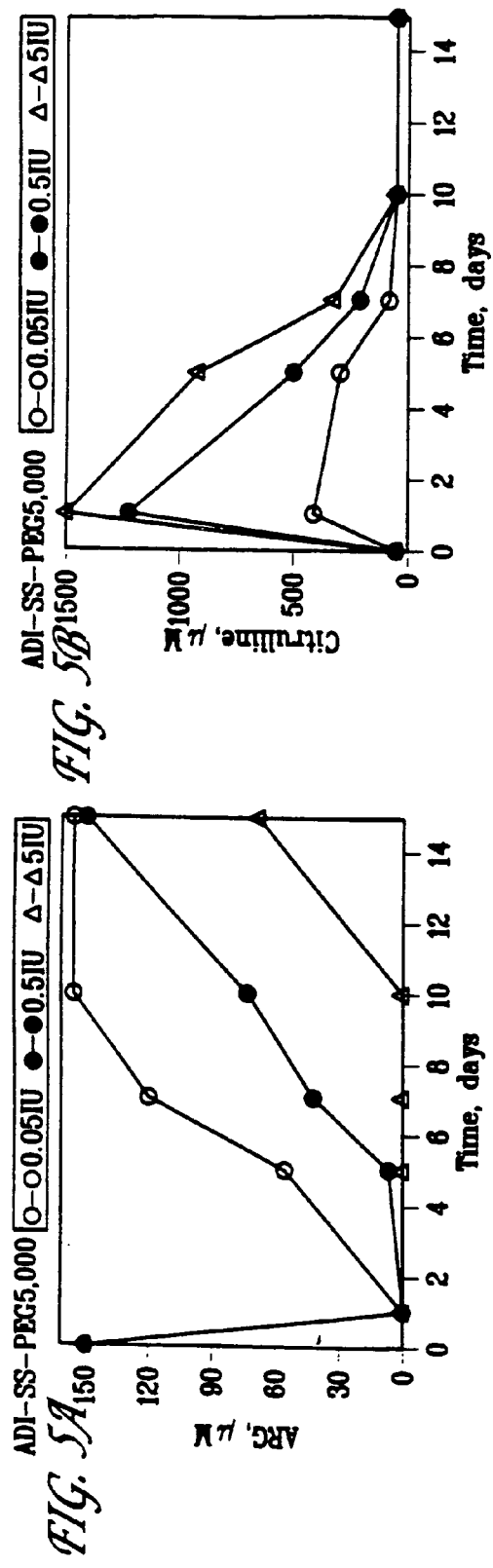
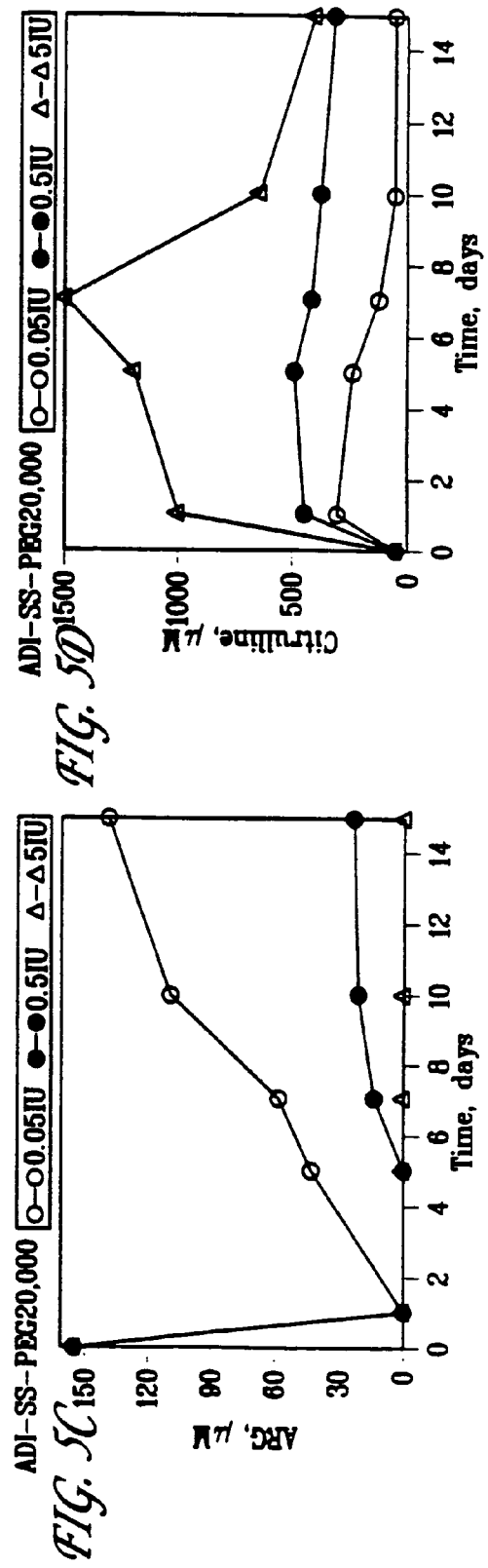
FIG. 5A
FIG. 5B
FIG. 5C
FIG. 5D

The alignment was done on 2 amino acid sequences.

Alignment

```
STRADIPYR    MTAQTPIHVVYSEIGKLKKVLLHRPGKEIENLMPDYLERLLFDDIPFLEDA       50
STRADIPNE    MSSHPIQVFSEIGKLKKVMLHRPGKELENLLPDYLERLLFDDIPFLEDAQ       50

STRADIPYR    QKEHDAFAQALRDEGIEVLYLETLAAESLVTPEIREAFIDEYLSEANIRG      100
STRADIPNE    KEHDAFAQALRDEGIEVLYLEQLAAESLTSPEIRDQFIEEYLDEANIRDR      100

STRADIPYR    RATKKAIRELLMAIEDNQELIEKTMAGVQKSELPEIPASEKGLTDLVESN      150
STRADIPNE    QTKVAIRELLHGIKDNQELVEKTMAGIQKVELPEIPDEAKDLTDLVESEY      150

STRADIPYR    YPFAIDPMPNLYFTRDPFATIGTGVSLNHMFSETRNRETLYGKYIFTHHP      200
STRADIPNE    PFAIDPMPNLYFTRDPFATIGNAVSLNHMFADTRNRETLYGKYIFKYHPI      200

STRADIPYR    IYGGGKVPMVYDRNETTRIEGGDELVLSKDVLAVGISQRTDAASIEKLLV      250
STRADIPNE    YGGKVDLVYNREEDTRIEGGDELVLSKDVLAVGISQRTDAASIEKLLVNI      250

STRADIPYR    NIFKQNLGFKKVLAFEFANNRKFMHLDTVFTMVDYDKFTIHPEIEGDLRV      300
STRADIPNE    FKKNVGFKKVLAFEFANNRKFMHLDTVFTMVDYDKFTIHPEIEGDLHVYS      300

STRADIPYR    YSVTYDNEELHIVEEKGDLAELLAANLGVEKVDLIRCGGDNLVAAGREQW      350
STRADIPNE    VTYENEKLKIVEEKGDLAELLAQNLGVEKVHLIRCGGGNIVAAAREQWND      350

STRADIPYR    NDGSNTLTIAPGVVVVYNRNTITNAILESKGLKLIKIHGSELVRGRGGPR      400
STRADIPNE    GSNTLTIAPGVVVVYDRNTVTNKILEEYGLRLIKIRGSELVRGRGGPRCM      400

STRADIPYR    CMSMPFEREDI                                              411
STRADIPNE    SMPFEREEV                                                409
```

STRADIPYR = *Streptococcus pyogenes*
STRADIPNE = *Streptococcus pneumoniae*

FIG. 10

The alignment was done on 2 amino acid sequences.

Alignment

| | | |
|---|---|---|
| BORADIBUR | MEEEYLNPINIFSEIGRLKKVLLHRPGEELENLTPLIMKNFLFDDIPYLK | 50 |
| BORADIAFZ | MEEYLNPINIFSEIGRLKKVLLHRPGEELENLTPFIMKNFLFDDIPYLEV | 50 |
| BORADIBUR | VARQEHEVFVNILKDNSVEIEYVEDLVSEVLASSVALKNKFISQFILEAE | 100 |
| BORADIAFZ | ARQEHEVFASILKNNLVEIEYIEDLISEVLVSSVALENKFISQFILEAEI | 100 |
| BORADIBUR | IKTDGVINILKDYFSNLTVDNMVSKMISGVAREELKDCEFSLDDWVNGSS | 150 |
| BORADIAFZ | KTDFTINLLKDYFSSLTIDNMISKMISGVVTEELKNYTSSLDDLVNGANL | 150 |
| BORADIBUR | FVIDPMPNVLFTRDPFASIGNGITINKMYTKVRRRETIFAEYIFKYHSAY | 200 |
| BORADIAFZ | FIIDPMPNVLFTRDPFASIGNGVTINKMFTKVRQRETIFAEYIFKYHPVY | 200 |
| BORADIBUR | KENVPIWFNRWEETSLEGGDEFVLNKDLLVIGISERTEAGSVEKLAASLF | 250 |
| BORADIAFZ | KENVPIWLNRWEEASLEGGDELVLNKGLLVIGISERTEAKSVEKLAISLF | 250 |
| BORADIBUR | KNKAPFSTILAFKIPKNRAYMHLDTVFTQIDYSVFTSFTSDDMYFSIYVL | 300 |
| BORADIAFZ | KNKTSFDTILAFQIPKNRSYMHLDTVFTQIDYSVFTSFTSDDMYFSIYVL | 300 |
| BORADIBUR | TYNSNSNKINIKKEKAKLKDVLSFYLGRKIDIIKCAGGDLIHGAREQWND | 350 |
| BORADIAFZ | TYNPSSSKIHIKKEKARIKDVLSFYLGRKIDIIKCAGGDLIHGAREQWND | 350 |
| BORADIBUR | GANVLAIAPGEVIAYSRNHVTNKLFEENGIKVHRIPSSELSRGRGGPRCM | 400 |
| BORADIAFZ | GANVLAIAPGEIIAYSRNHVTNKLFEENGIKVHRIPSSELSRGRGGPRCM | 400 |
| BORADIBUR | SMSLVREDI | 409 |
| BORADIAFZ | SMPLIREDI | 409 |

BORADIBUR = *Borrelia burgdorferi*
BORADIAFZ = *Borrelia afzellii*

FIG. 11

The alignment was done on 3 amino acid sequences.

Alignment

| | | |
|---|---|---|
| QIAADIINT | MTDFSKDKEKLAQATQGGENERAEIVVVHLPQGTSFLTSLNPEGNLLEEP | 50 |
| CLOADIPER | MRDDRALNVTSEIGRLKTVLLHRPGEEIENLTPDLLDRLLFDDIPYLKVA | 50 |
| BACADILIC | MIMTTPIHVYSEIGPLKTVMLKRPGRELENLTPEYLERLLFDDIPFLPAV | 50 |
| QIAADIINT | ICPDELRRDHEGFQAVLKEKGCRVYMPYDVLSEASPAEREVLMDQAMASL | 100 |
| CLOADIPER | REEHDAFAQTLREAGVEVLYLEVLAAEAIETSDEVKQQFISEFIDEAGVE | 100 |
| BACADILIC | QKEHDQFAETLKQQGAEVLYLEKLTAEALDDALVREQFIDELLTESKADI | 100 |
| QIAADIINT | KYELHATGARITPKMKYCVSDEYKRKVLSALSTRNLVDVILSEPVIHLAP | 150 |
| CLOADIPER | SERLKEALIEYFNSFSDNKAMVDKMMAGVRKEELKDYHRESLYDQVNNVY | 150 |
| BACADILIC | NGAYDRLKEFLLTFDADSMVEQVMSGIRKNELEREKKSHLHELMEDHYPF | 150 |
| QIAADIINT | GVRNTALVTNSVEIHDSNNMVFMRDQQITTRRGIVMGQFQAPQRRREQVL | 200 |
| CLOADIPER | PFVCDPMPNLYFTREPFATIGHGITLNHMRTDTRNRETIFAKYIFRHHPR | 200 |
| BACADILIC | YLDPMPNLYFTRDPAAAIGSGLTINKMKEPARRRESLFMRYIINHHPRFK | 200 |
| QIAADIINT | ALIFWKRLGARVVGDCREGGPHCMLEGGDFVPVSPGLAMMGVGLRSTYVG | 250 |
| CLOADIPER | FEGKDIPFWFNRNDKTSLEGGDELILSKEILAVGISQRTDSASVEKLAKK | 250 |
| BACADILIC | GHEIPVWLDRDFKFNIEGGDELVLNEETVAIGVSERTTAQAIERLVRNLF | 250 |
| QIAADIINT | AQYLMSKDLLGTRRFAVVKDCFDQHQDRMHLDCTFSVLHDKLVVLDDYIC | 300 |
| CLOADIPER | LLYYPDTSFKTVLAFKIPVSRAFMHLDTVFTQVDYDKFTVHPGIVGPLEV | 300 |
| BACADILIC | QRQSRIRRVLAVEIPKSRAFMHLDTVFTMVDRDQFTIHPAIQGPEGDMRI | 300 |
| QIAADIINT | SGMGLRYVDEWIDVGADAVKKAKSSAVTCGNYVLAKANVEFQQWLSENGY | 350 |
| CLOADIPER | YALTKDPENDGQLLVTEEVDTLENILKKYLDRDIKLIKCGGGDEIIAARE | 350 |
| BACADILIC | FVLERGKTADEIHTTEEHNLPEVLKRTLGLSDVNLIFCGGGDEIASAREQ | 350 |
| QIAADIINT | TIVRIPHEYQLAYGCNNLNLGNNCVLSVHQPTVDFIKADPAYISYCKSNN | 400 |
| CLOADIPER | QWNDGSNTLAIAPGEVVVYSRNYVTNEILEKEGIKLHVIPSSELSRGRGG | 400 |
| BACADILIC | WNDGSNTLAIAPGVVVTYDRNYISNECLREQGIKVIEIPSGELSRGRGGP | 400 |
| QIAADIINT | LPNGLDLVYVPFRGITRMYGSLHCASQVVYRTPLAPAAVKACEQEGDGIA | 450 |
| CLOADIPER | PRCMSMPLIREDL | 413 |
| BACADILIC | RCMSMPLYREDVK | 413 |
| QIAADIINT | AIYEKNGEPVDAAGKKFDCVIYIPSSVDDLIDGLKINLRDDAAPSREIIA | 500 |
| QIAADIINT | DAYGLYQKLVSEGRVPYITWRMPSMPVVSLKGAAKAGSLKAVLDKIPQLT | 550 |
| QIAADIINT | PFTPKAVEGAPAAYTRYLGLEQADICVDIK | 580 |

QIAADIINT = *Qiardia intestinalis*
CLOADIPER = *Clostridium perfringens*
BACADILIC = *Bacillus licheniformis*

FIG. 12

The alignment was done on 2 amino acid sequences.

Alignment

```
ENTADIFAE  MSHPINVFSEIGKLKTVMLHRPGKELENLMPDYLERLLFDDIPFLEKAQA          50
LACADISAK  MTSPIHVNSEIGKLKTVLLKRPGKEVENITPDIMYRLLFDDIPYLPTIQK          50

ENTADIFAE  EHDAFAELLRSKDIEVVYLEDLAAEALINEEVRRQFIDQFLEEANIRSES          100
LACADISAK  EHDQFAQTLRDNGVEVLYLENLAAEAIDAGDVKEAFLDKMLNESHIKSPQ          100

ENTADIFAE  AKEKVRELMLEIDDNEELIQKAIAGIQKQELPKYEQEFLTDMVEADYPFI          150
LACADISAK  VQAALKDYLISMATLDMVEKIMAGVRTNEIDIKSKALIDVSADDDYPFYM          150

ENTADIFAE  IDPMPNLYFTRDNFATMGHGISLNHMYSVTRQRETIFGQYIFDYHPRFAG          200
LACADISAK  DPMPNLYFTRDPAASMGDGLTINKMTFEARQRESMFMEVIMQHHPRFANQ          200

ENTADIFAE  KEVPRVYDRSESTRIEGGDELILSKEVVAIGISQRTDAASIEKIARNIFE          250
LACADISAK  GAQVWRDRDHIDRMEGGDELILSDKVLAIGISQRTSAQSIEELAKVLFAN          250

ENTADIFAE  QKLGFKNILAFDIGEHRKFMHLDTVFTMIDYDKFTIHPEIEGGLVVYSIT          300
LACADISAK  HSGFEKILAIKIPHKHAMMHLDTVFTMIDYDKFTIHPGIQGAGGMVDTYI          300

ENTADIFAE  EKADGDIQITKEKDTLDNILCKYLHLDNVQLIRCGAGNLTAAAREQWNDG          350
LACADISAK  LEPGNNDEIKITHQTDLEKVLRDALEVPELTLIPCGGGDAVVAPREQWND          350

ENTADIFAE  SNTLAIAPGEVVVYDRNTITNKALEEAGVKLNYIPGSELVRGRGGPRCMS          400
LACADISAK  GSNTLAIAPGVVVTYDRNYVSNENLRQYGIKVIEVPSSELSRGRGGPRCM          400

ENTADIFAE  MPLYREDL                                                    408
LACADISAK  SMPLVRRKT                                                   409
```

ENTADIFAE = *Enterococcus faecalis*
LACADISAK = *Lactobacillus sake*

FIG. 13

SEQUENCE LISTING

<160> NUMBER OF SEQ ID NOS: 14

<210> SEQ ID NO 1
<211> LENGTH: 410

```
<212> TYPE: PRT
<213> ORGANISM: Mycoplasma arginini

<400> SEQUENCE: 1

Met Ser Val Phe Asp Ser Lys Phe Lys Gly Ile His Val Tyr Ser Glu
 1               5                  10                  15

Ile Gly Glu Leu Glu Ser Val Leu Val His Glu Pro Gly Arg Glu Ile
             20                  25                  30

Asp Tyr Ile Thr Pro Ala Arg Leu Asp Glu Leu Leu Phe Ser Ala Ile
         35                  40                  45

Leu Glu Ser His Asp Ala Arg Lys Glu His Lys Gln Phe Val Ala Glu
     50                  55                  60

Leu Lys Ala Asn Asp Ile Asn Val Val Glu Leu Ile Asp Leu Val Ala
 65                  70                  75                  80

Glu Thr Tyr Asp Leu Ala Ser Gln Glu Ala Lys Asp Lys Leu Ile Glu
                 85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Lys Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400
```

```
Met Pro Leu Ser Arg Lys Asp Val Lys Trp
                405                 410
```

<210> SEQ ID NO 2
<211> LENGTH: 410
<212> TYPE: PRT
<213> ORGANISM: Mycoplasma arthritidis

<400> SEQUENCE: 2

```
Met Ser Val Phe Asp Ser Lys Phe Lys Gly Ile His Val Tyr Ser Glu
 1               5                  10                  15

Ile Gly Glu Leu Glu Ser Val Leu Val His Glu Pro Gly Arg Glu Ile
             20                  25                  30

Asp Tyr Ile Thr Pro Ala Arg Leu Asp Glu Leu Leu Phe Ser Ala Ile
             35                  40                  45

Leu Glu Ser His Asp Ala Arg Lys Glu Gln Ser Gln Phe Val Ala Ile
         50                  55                  60

Leu Lys Ala Asn Asp Ile Asn Val Val Glu Thr Ile Asp Leu Val Ala
 65                  70                  75                  80

Glu Thr Tyr Asp Leu Ala Ser Gln Glu Ala Lys Asp Arg Leu Ile Glu
                 85                  90                  95

Glu Phe Leu Glu Asp Ser Glu Pro Val Leu Ser Glu Ala His Lys Lys
            100                 105                 110

Val Val Arg Asn Phe Leu Lys Ala Lys Lys Thr Ser Arg Lys Leu Val
        115                 120                 125

Glu Leu Met Met Ala Gly Ile Thr Lys Tyr Asp Leu Gly Val Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Phe Met Arg
                165                 170                 175

Tyr Lys Val Arg Arg Arg Glu Thr Leu Phe Ser Arg Phe Val Phe Arg
            180                 185                 190

Asn His Pro Lys Leu Val Asn Thr Pro Trp Tyr Tyr Asp Pro Ala Met
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Asp Thr Val Thr Leu
225                 230                 235                 240

Leu Ala Lys Asn Leu Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asn Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Lys Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Ile Ala Ile Arg Pro Gly Val Val Ile Gly Tyr Ser Arg Asn Glu
```

-continued

```
                355                 360                 365
Lys Thr Asn Ala Ala Leu Lys Ala Ala Gly Ile Lys Val Leu Pro Phe
        370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 3
<211> LENGTH: 409
<212> TYPE: PRT
<213> ORGANISM: Mycoplasma hominis

<400> SEQUENCE: 3

Met Ser Val Phe Asp Ser Lys Phe Asn Gly Ile His Val Tyr Ser Glu
 1               5                  10                  15

Ile Gly Glu Leu Glu Thr Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Gln Ser Phe Val Lys Ile
        50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
                85                  90                  95

Thr Phe Leu Glu Glu Thr Val Pro Val Leu Thr Glu Ala Asn Lys Lys
            100                 105                 110

Ala Val Arg Ala Phe Leu Leu Ser Lys Pro Thr His Glu Met Val Glu
        115                 120                 125

Phe Met Met Ser Gly Ile Thr Lys Tyr Glu Leu Gly Val Glu Ser Glu
130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
        195                 200                 205

Met Pro Ile Glu Gly Gly Asp Val Phe Ile Tyr Asn Asn Glu Thr Leu
210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
        275                 280                 285

Asp Val Phe Lys Phe Trp Asp Tyr Asp Leu Val Asn Gly Gly Ala Glu
        290                 295                 300

Pro Gln Pro Gln Leu Asn Gly Leu Pro Leu Asp Lys Leu Leu Ala Ser
305                 310                 315                 320
```

-continued

```
Ile Ile Asn Lys Glu Pro Val Leu Ile Pro Ile Gly Gly Ala Gly Ala
            325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
            355                 360                 365

Thr Asn Ala Ala Leu Lys Ala Ala Gly Ile Thr Val Leu Pro Phe His
        370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405
```

<210> SEQ ID NO 4
<211> LENGTH: 23
<212> TYPE: DNA
<213> ORGANISM: Mycoplasma arginini

<400> SEQUENCE: 4
gcaatcgatg tgtatttgac agt                                     23

<210> SEQ ID NO 5
<211> LENGTH: 33
<212> TYPE: DNA
<213> ORGANISM: Mycoplasma arginini

<400> SEQUENCE: 5
tgaggatcct tactaccact taacatcttt acg                           33

<210> SEQ ID NO 6
<211> LENGTH: 411
<212> TYPE: PRT
<213> ORGANISM: Steptococcus pyogenes

<400> SEQUENCE: 6

```
Met Thr Ala Gln Thr Pro Ile His Val Tyr Ser Glu Ile Gly Lys Leu
  1               5                  10                  15

Lys Lys Val Leu Leu His Arg Pro Gly Lys Glu Ile Glu Asn Leu Met
                20                  25                  30

Pro Asp Tyr Leu Glu Arg Leu Leu Phe Asp Asp Ile Pro Phe Leu Glu
            35                  40                  45

Asp Ala Gln Lys Glu His Asp Ala Phe Ala Gln Ala Leu Arg Asp Glu
        50                  55                  60

Gly Ile Glu Val Leu Tyr Leu Glu Thr Leu Ala Ala Glu Ser Leu Val
 65                  70                  75                  80

Thr Pro Glu Ile Arg Glu Ala Phe Ile Asp Glu Tyr Leu Ser Glu Ala
                85                  90                  95

Asn Ile Arg Gly Arg Ala Thr Lys Lys Ala Ile Arg Glu Leu Leu Met
            100                 105                 110

Ala Ile Glu Asp Asn Gln Glu Leu Ile Glu Lys Thr Met Ala Gly Val
        115                 120                 125

Gln Lys Ser Glu Leu Pro Glu Ile Pro Ala Ser Glu Lys Gly Leu Thr
    130                 135                 140

Asp Leu Val Glu Ser Asn Tyr Pro Phe Ala Ile Asp Pro Met Pro Asn
145                 150                 155                 160

Leu Tyr Phe Thr Arg Asp Pro Phe Ala Thr Ile Gly Thr Gly Val Ser
                165                 170                 175
```

-continued

```
Leu Asn His Met Phe Ser Glu Thr Arg Asn Arg Glu Thr Leu Tyr Gly
            180                 185                 190

Lys Tyr Ile Phe Thr His His Pro Ile Tyr Gly Gly Lys Val Pro
        195                 200                 205

Met Val Tyr Asp Arg Asn Glu Thr Thr Arg Ile Glu Gly Gly Asp Glu
    210                 215                 220

Leu Val Leu Ser Lys Asp Val Leu Ala Val Gly Ile Ser Gln Arg Thr
225                 230                 235                 240

Asp Ala Ala Ser Ile Glu Lys Leu Leu Val Asn Ile Phe Lys Gln Asn
                245                 250                 255

Leu Gly Phe Lys Lys Val Leu Ala Phe Glu Phe Ala Asn Asn Arg Lys
            260                 265                 270

Phe Met His Leu Asp Thr Val Phe Thr Met Val Asp Tyr Asp Lys Phe
        275                 280                 285

Thr Ile His Pro Glu Ile Glu Gly Asp Leu Arg Val Tyr Ser Val Thr
    290                 295                 300

Tyr Asp Asn Glu Glu Leu His Ile Val Glu Glu Lys Gly Asp Leu Ala
305                 310                 315                 320

Glu Leu Leu Ala Ala Asn Leu Gly Val Glu Lys Val Asp Leu Ile Arg
                325                 330                 335

Cys Gly Gly Asp Asn Leu Val Ala Ala Gly Arg Glu Gln Trp Asn Asp
            340                 345                 350

Gly Ser Asn Thr Leu Thr Ile Ala Pro Gly Val Val Val Tyr Asn
        355                 360                 365

Arg Asn Thr Ile Thr Asn Ala Ile Leu Glu Ser Lys Gly Leu Lys Leu
    370                 375                 380

Ile Lys Ile His Gly Ser Glu Leu Val Arg Gly Arg Gly Pro Arg
385                 390                 395                 400

Cys Met Ser Met Pro Phe Glu Arg Glu Asp Ile
                405                 410

<210> SEQ ID NO 7
<211> LENGTH: 409
<212> TYPE: PRT
<213> ORGANISM: Steptococcus pneumoniae

<400> SEQUENCE: 7

Met Ser Ser His Pro Ile Gln Val Phe Ser Glu Ile Gly Lys Leu Lys
1               5                   10                  15

Lys Val Met Leu His Arg Pro Gly Lys Glu Leu Glu Asn Leu Leu Pro
            20                  25                  30

Asp Tyr Leu Glu Arg Leu Leu Phe Asp Asp Ile Pro Phe Leu Glu Asp
        35                  40                  45

Ala Gln Lys Glu His Asp Ala Phe Ala Gln Ala Leu Arg Asp Glu Gly
    50                  55                  60

Ile Glu Val Leu Tyr Leu Glu Gln Leu Ala Ala Glu Ser Leu Thr Ser
65                  70                  75                  80

Pro Glu Ile Arg Asp Gln Phe Ile Glu Glu Tyr Leu Asp Glu Ala Asn
                85                  90                  95

Ile Arg Asp Arg Gln Thr Lys Val Ala Ile Arg Glu Leu Leu His Gly
            100                 105                 110

Ile Lys Asp Asn Gln Glu Leu Val Glu Lys Thr Met Ala Gly Ile Gln
        115                 120                 125

Lys Val Glu Leu Pro Glu Ile Pro Asp Glu Ala Lys Asp Leu Thr Asp
    130                 135                 140
```

```
Leu Val Glu Ser Glu Tyr Pro Phe Ala Ile Asp Pro Met Pro Asn Leu
145                 150                 155                 160

Tyr Phe Thr Arg Asp Pro Phe Ala Thr Ile Gly Asn Ala Val Ser Leu
            165                 170                 175

Asn His Met Phe Ala Asp Thr Arg Asn Arg Glu Thr Leu Tyr Gly Lys
                180                 185                 190

Tyr Ile Phe Lys Tyr His Pro Ile Tyr Gly Gly Lys Val Asp Leu Val
            195                 200                 205

Tyr Asn Arg Glu Glu Asp Thr Arg Ile Glu Gly Asp Glu Leu Val
210                 215                 220

Leu Ser Lys Asp Val Leu Ala Val Gly Ile Ser Gln Arg Thr Asp Ala
225                 230                 235                 240

Ala Ser Ile Glu Lys Leu Leu Val Asn Ile Phe Lys Lys Asn Val Gly
                245                 250                 255

Phe Lys Lys Val Leu Ala Phe Glu Phe Ala Asn Asn Arg Lys Phe Met
            260                 265                 270

His Leu Asp Thr Val Phe Thr Met Val Asp Tyr Asp Lys Phe Thr Ile
            275                 280                 285

His Pro Glu Ile Glu Gly Asp Leu His Val Tyr Ser Val Thr Tyr Glu
290                 295                 300

Asn Glu Lys Leu Lys Ile Val Glu Glu Lys Gly Asp Leu Ala Glu Leu
305                 310                 315                 320

Leu Ala Gln Asn Leu Gly Val Glu Lys Val His Leu Ile Arg Cys Gly
                325                 330                 335

Gly Gly Asn Ile Val Ala Ala Arg Glu Gln Trp Asn Asp Gly Ser
                340                 345                 350

Asn Thr Leu Thr Ile Ala Pro Gly Val Val Val Tyr Asp Arg Asn
                355                 360                 365

Thr Val Thr Asn Lys Ile Leu Glu Glu Tyr Gly Leu Arg Leu Ile Lys
        370                 375                 380

Ile Arg Gly Ser Glu Leu Val Arg Gly Arg Gly Pro Arg Cys Met
385                 390                 395                 400

Ser Met Pro Phe Glu Arg Glu Val
                405

<210> SEQ ID NO 8
<211> LENGTH: 410
<212> TYPE: PRT
<213> ORGANISM: Borrelia burgdorferi

<400> SEQUENCE: 8

Met Glu Glu Glu Tyr Leu Asn Pro Ile Asn Ile Phe Ser Glu Ile Gly
1               5                   10                  15

Arg Leu Lys Lys Val Leu Leu His Arg Pro Gly Glu Glu Leu Glu Asn
            20                  25                  30

Leu Thr Pro Leu Ile Met Lys Asn Phe Leu Phe Asp Asp Ile Pro Tyr
        35                  40                  45

Leu Lys Val Ala Arg Gln Glu His Glu Val Phe Val Asn Ile Leu Lys
    50                  55                  60

Asp Asn Ser Val Glu Ile Glu Tyr Val Glu Asp Leu Val Ser Glu Val
65                  70                  75                  80

Leu Ala Ser Ser Val Ala Leu Lys Asn Lys Phe Ile Ser Gln Phe Ile
                85                  90                  95

Leu Glu Ala Glu Ile Lys Thr Asp Gly Val Ile Asn Ile Leu Lys Asp
```

-continued

```
            100                 105                 110
Tyr Phe Ser Asn Leu Thr Val Asp Asn Met Val Ser Lys Met Ile Ser
        115                 120                 125

Gly Val Ala Arg Glu Glu Leu Lys Asp Cys Glu Phe Ser Leu Asp Asp
    130                 135                 140

Trp Val Asn Gly Ser Ser Leu Phe Val Ile Asp Pro Met Pro Asn Val
145                 150                 155                 160

Leu Phe Thr Arg Asp Pro Phe Ala Ser Ile Gly Asn Gly Ile Thr Ile
                165                 170                 175

Asn Lys Met Tyr Thr Lys Val Arg Arg Arg Glu Thr Ile Phe Ala Glu
            180                 185                 190

Tyr Ile Phe Lys Tyr His Ser Ala Tyr Lys Glu Asn Val Pro Ile Trp
        195                 200                 205

Phe Asn Arg Trp Glu Glu Thr Ser Leu Glu Gly Gly Asp Glu Phe Val
    210                 215                 220

Leu Asn Lys Asp Leu Leu Val Ile Gly Ile Ser Glu Arg Thr Glu Ala
225                 230                 235                 240

Gly Ser Val Glu Lys Leu Ala Ala Ser Leu Phe Lys Asn Lys Ala Pro
                245                 250                 255

Phe Ser Thr Ile Leu Ala Phe Lys Ile Pro Lys Asn Arg Ala Tyr Met
            260                 265                 270

His Leu Asp Thr Val Phe Thr Gln Ile Asp Tyr Ser Val Phe Thr Ser
        275                 280                 285

Phe Thr Ser Asp Asp Met Tyr Phe Ser Ile Tyr Val Leu Thr Tyr Asn
    290                 295                 300

Ser Asn Ser Asn Lys Ile Asn Ile Lys Lys Glu Lys Ala Lys Leu Lys
305                 310                 315                 320

Asp Val Leu Ser Phe Tyr Leu Gly Arg Lys Ile Asp Ile Ile Lys Cys
                325                 330                 335

Ala Gly Gly Asp Leu Ile His Gly Ala Arg Glu Gln Trp Asn Asp Gly
            340                 345                 350

Ala Asn Val Leu Ala Ile Ala Pro Gly Glu Val Ile Ala Tyr Ser Arg
        355                 360                 365

Asn His Val Thr Asn Lys Leu Phe Glu Glu Asn Gly Ile Lys Val His
    370                 375                 380

Arg Ile Pro Ser Ser Glu Leu Ser Arg Gly Arg Gly Gly Pro Arg Cys
385                 390                 395                 400

Met Ser Met Ser Leu Val Arg Glu Asp Ile
                405                 410

<210> SEQ ID NO 9
<211> LENGTH: 409
<212> TYPE: PRT
<213> ORGANISM: Borrelia afzelii

<400> SEQUENCE: 9

Met Glu Glu Tyr Leu Asn Pro Ile Asn Ile Phe Ser Glu Ile Gly Arg
  1               5                  10                  15

Leu Lys Lys Val Leu Leu His Arg Pro Gly Glu Glu Leu Glu Asn Leu
             20                  25                  30

Thr Pro Phe Ile Met Lys Asn Phe Leu Phe Asp Asp Ile Pro Tyr Leu
         35                  40                  45

Glu Val Ala Arg Gln Glu His Glu Val Phe Ala Ser Ile Leu Lys Asn
     50                  55                  60
```

```
Asn Leu Val Glu Ile Glu Tyr Ile Glu Asp Leu Ile Ser Glu Val Leu
 65                  70                  75                  80

Val Ser Ser Val Ala Leu Glu Asn Lys Phe Ile Ser Gln Phe Ile Leu
                 85                  90                  95

Glu Ala Glu Ile Lys Thr Asp Phe Thr Ile Asn Leu Leu Lys Asp Tyr
            100                 105                 110

Phe Ser Ser Leu Thr Ile Asp Asn Met Ile Ser Lys Met Ile Ser Gly
            115                 120                 125

Val Val Thr Glu Glu Leu Lys Asn Tyr Thr Ser Ser Leu Asp Asp Leu
        130                 135                 140

Val Asn Gly Ala Asn Leu Phe Ile Ile Asp Pro Met Pro Asn Val Leu
145                 150                 155                 160

Phe Thr Arg Asp Pro Phe Ala Ser Ile Gly Asn Gly Val Thr Ile Asn
                165                 170                 175

Lys Met Phe Thr Lys Val Arg Gln Arg Glu Thr Ile Phe Ala Glu Tyr
            180                 185                 190

Ile Phe Lys Tyr His Pro Val Tyr Lys Glu Asn Val Pro Ile Trp Leu
        195                 200                 205

Asn Arg Trp Glu Glu Ala Ser Leu Glu Gly Gly Asp Glu Leu Val Leu
        210                 215                 220

Asn Lys Gly Leu Leu Val Ile Gly Ile Ser Glu Arg Thr Glu Ala Lys
225                 230                 235                 240

Ser Val Glu Lys Leu Ala Ile Ser Leu Phe Lys Asn Lys Thr Ser Phe
                245                 250                 255

Asp Thr Ile Leu Ala Phe Gln Ile Pro Lys Asn Arg Ser Tyr Met His
            260                 265                 270

Leu Asp Thr Val Phe Thr Gln Ile Asp Tyr Ser Val Phe Thr Ser Phe
        275                 280                 285

Thr Ser Asp Asp Met Tyr Phe Ser Ile Tyr Val Leu Thr Tyr Asn Pro
290                 295                 300

Ser Ser Ser Lys Ile His Ile Lys Lys Glu Lys Ala Arg Ile Lys Asp
305                 310                 315                 320

Val Leu Ser Phe Tyr Leu Gly Arg Lys Ile Asp Ile Ile Lys Cys Ala
                325                 330                 335

Gly Gly Asp Leu Ile His Gly Ala Arg Glu Gln Trp Asn Asp Gly Ala
            340                 345                 350

Asn Val Leu Ala Ile Ala Pro Gly Glu Ile Ile Ala Tyr Ser Arg Asn
        355                 360                 365

His Val Thr Asn Lys Leu Phe Glu Glu Asn Gly Ile Lys Val His Arg
        370                 375                 380

Ile Pro Ser Ser Glu Leu Ser Arg Gly Arg Gly Pro Arg Cys Met
385                 390                 395                 400

Ser Met Pro Leu Ile Arg Glu Asp Ile
                405

<210> SEQ ID NO 10
<211> LENGTH: 580
<212> TYPE: PRT
<213> ORGANISM: Qiardia intestinalis

<400> SEQUENCE: 10

Met Thr Asp Phe Ser Lys Asp Lys Glu Lys Leu Ala Gln Ala Thr Gln
  1               5                  10                  15

Gly Gly Glu Asn Glu Arg Ala Glu Ile Val Val Val His Leu Pro Gln
             20                  25                  30
```

```
Gly Thr Ser Phe Leu Thr Ser Leu Asn Pro Glu Gly Asn Leu Leu Glu
            35                  40                  45

Glu Pro Ile Cys Pro Asp Glu Leu Arg Arg Asp His Glu Gly Phe Gln
        50                  55                  60

Ala Val Leu Lys Glu Lys Gly Cys Arg Val Tyr Met Pro Tyr Asp Val
65                  70                  75                  80

Leu Ser Glu Ala Ser Pro Ala Glu Arg Glu Val Leu Met Asp Gln Ala
                85                  90                  95

Met Ala Ser Leu Lys Tyr Glu Leu His Ala Thr Gly Ala Arg Ile Thr
            100                 105                 110

Pro Lys Met Lys Tyr Cys Val Ser Asp Glu Tyr Lys Arg Lys Val Leu
        115                 120                 125

Ser Ala Leu Ser Thr Arg Asn Leu Val Asp Val Ile Leu Ser Glu Pro
130                 135                 140

Val Ile His Leu Ala Pro Gly Val Arg Asn Thr Ala Leu Val Thr Asn
145                 150                 155                 160

Ser Val Glu Ile His Asp Ser Asn Asn Met Val Phe Met Arg Asp Gln
                165                 170                 175

Gln Ile Thr Thr Arg Arg Gly Ile Val Met Gly Gln Phe Gln Ala Pro
            180                 185                 190

Gln Arg Arg Glu Gln Val Leu Ala Leu Ile Phe Trp Lys Arg Leu
        195                 200                 205

Gly Ala Arg Val Val Gly Asp Cys Arg Glu Gly Pro His Cys Met
210                 215                 220

Leu Glu Gly Gly Asp Phe Val Pro Val Ser Pro Gly Leu Ala Met Met
225                 230                 235                 240

Gly Val Gly Leu Arg Ser Thr Tyr Val Gly Ala Gln Tyr Leu Met Ser
                245                 250                 255

Lys Asp Leu Leu Gly Thr Arg Arg Phe Ala Val Val Lys Asp Cys Phe
            260                 265                 270

Asp Gln His Gln Asp Arg Met His Leu Asp Cys Thr Phe Ser Val Leu
        275                 280                 285

His Asp Lys Leu Val Val Leu Asp Asp Tyr Ile Cys Ser Gly Met Gly
290                 295                 300

Leu Arg Tyr Val Asp Glu Trp Ile Asp Val Gly Ala Asp Ala Val Lys
305                 310                 315                 320

Lys Ala Lys Ser Ser Ala Val Thr Cys Gly Asn Tyr Val Leu Ala Lys
                325                 330                 335

Ala Asn Val Glu Phe Gln Gln Trp Leu Ser Glu Asn Gly Tyr Thr Ile
            340                 345                 350

Val Arg Ile Pro His Glu Tyr Gln Leu Ala Tyr Gly Cys Asn Asn Leu
        355                 360                 365

Asn Leu Gly Asn Cys Val Leu Ser Val His Gln Pro Thr Val Asp
370                 375                 380

Phe Ile Lys Ala Asp Pro Ala Tyr Ile Ser Tyr Cys Lys Ser Asn Asn
385                 390                 395                 400

Leu Pro Asn Gly Leu Asp Leu Val Tyr Val Pro Phe Arg Gly Ile Thr
                405                 410                 415

Arg Met Tyr Gly Ser Leu His Cys Ala Ser Gln Val Val Tyr Arg Thr
            420                 425                 430

Pro Leu Ala Pro Ala Ala Val Lys Ala Cys Glu Gln Glu Gly Asp Gly
        435                 440                 445
```

Ile Ala Ala Ile Tyr Glu Lys Asn Gly Glu Pro Val Asp Ala Gly
        450                 455                 460

Lys Lys Phe Asp Cys Val Ile Tyr Ile Pro Ser Ser Val Asp Asp Leu
465                 470                 475                 480

Ile Asp Gly Leu Lys Ile Asn Leu Arg Asp Asp Ala Ala Pro Ser Arg
                485                 490                 495

Glu Ile Ile Ala Asp Ala Tyr Gly Leu Tyr Gln Lys Leu Val Ser Glu
            500                 505                 510

Gly Arg Val Pro Tyr Ile Thr Trp Arg Met Pro Ser Met Pro Val Val
        515                 520                 525

Ser Leu Lys Gly Ala Ala Lys Ala Gly Ser Leu Lys Ala Val Leu Asp
        530                 535                 540

Lys Ile Pro Gln Leu Thr Pro Phe Thr Pro Lys Ala Val Glu Gly Ala
545                 550                 555                 560

Pro Ala Ala Tyr Thr Arg Tyr Leu Gly Leu Glu Gln Ala Asp Ile Cys
                565                 570                 575

Val Asp Ile Lys
            580

<210> SEQ ID NO 11
<211> LENGTH: 413
<212> TYPE: PRT
<213> ORGANISM: Clostridium perfringens

<400> SEQUENCE: 11

Met Arg Asp Asp Arg Ala Leu Asn Val Thr Ser Glu Ile Gly Arg Leu
1               5                   10                  15

Lys Thr Val Leu Leu His Arg Pro Gly Glu Glu Ile Glu Asn Leu Thr
            20                  25                  30

Pro Asp Leu Leu Asp Arg Leu Leu Phe Asp Asp Ile Pro Tyr Leu Lys
        35                  40                  45

Val Ala Arg Glu Glu His Asp Ala Phe Ala Gln Thr Leu Arg Glu Ala
    50                  55                  60

Gly Val Glu Val Leu Tyr Leu Glu Val Leu Ala Ala Glu Ala Ile Glu
65                  70                  75                  80

Thr Ser Asp Glu Val Lys Gln Gln Phe Ile Ser Glu Phe Ile Asp Glu
                85                  90                  95

Ala Gly Val Glu Ser Glu Arg Leu Lys Glu Ala Leu Ile Glu Tyr Phe
            100                 105                 110

Asn Ser Phe Ser Asp Asn Lys Ala Met Val Asp Lys Met Met Ala Gly
        115                 120                 125

Val Arg Lys Glu Glu Leu Lys Asp Tyr His Arg Glu Ser Leu Tyr Asp
130                 135                 140

Gln Val Asn Asn Val Tyr Pro Phe Val Cys Asp Pro Met Pro Asn Leu
145                 150                 155                 160

Tyr Phe Thr Arg Glu Pro Phe Ala Thr Ile Gly His Gly Ile Thr Leu
                165                 170                 175

Asn His Met Arg Thr Asp Thr Arg Asn Arg Glu Thr Ile Phe Ala Lys
            180                 185                 190

Tyr Ile Phe Arg His His Pro Arg Phe Glu Gly Lys Asp Ile Pro Phe
        195                 200                 205

Trp Phe Asn Arg Asn Asp Lys Thr Ser Leu Glu Gly Gly Asp Glu Leu
    210                 215                 220

Ile Leu Ser Lys Glu Ile Leu Ala Val Gly Ile Ser Gln Arg Thr Asp
225                 230                 235                 240

```
Ser Ala Ser Val Glu Lys Leu Ala Lys Lys Leu Leu Tyr Tyr Pro Asp
            245                 250                 255

Thr Ser Phe Lys Thr Val Leu Ala Phe Lys Ile Pro Val Ser Arg Ala
            260                 265                 270

Phe Met His Leu Asp Thr Val Phe Thr Gln Val Asp Tyr Asp Lys Phe
            275                 280                 285

Thr Val His Pro Gly Ile Val Gly Pro Leu Glu Val Tyr Ala Leu Thr
            290                 295                 300

Lys Asp Pro Glu Asn Asp Gly Gln Leu Leu Val Thr Glu Glu Val Asp
305                 310                 315                 320

Thr Leu Glu Asn Ile Leu Lys Lys Tyr Leu Asp Arg Asp Ile Lys Leu
            325                 330                 335

Ile Lys Cys Gly Gly Asp Glu Ile Ile Ala Ala Arg Glu Gln Trp
            340                 345                 350

Asn Asp Gly Ser Asn Thr Leu Ala Ile Ala Pro Gly Glu Val Val Val
            355                 360                 365

Tyr Ser Arg Asn Tyr Val Thr Asn Glu Ile Leu Glu Lys Glu Gly Ile
            370                 375                 380

Lys Leu His Val Ile Pro Ser Ser Glu Leu Ser Arg Gly Arg Gly Gly
385                 390                 395                 400

Pro Arg Cys Met Ser Met Pro Leu Ile Arg Glu Asp Leu
            405                 410

<210> SEQ ID NO 12
<211> LENGTH: 413
<212> TYPE: PRT
<213> ORGANISM: Bacillus licheniformis

<400> SEQUENCE: 12

Met Ile Met Thr Thr Pro Ile His Val Tyr Ser Glu Ile Gly Pro Leu
1               5                   10                  15

Lys Thr Val Met Leu Lys Arg Pro Gly Arg Glu Leu Glu Asn Leu Thr
            20                  25                  30

Pro Glu Tyr Leu Glu Arg Leu Leu Phe Asp Asp Ile Pro Phe Leu Pro
            35                  40                  45

Ala Val Gln Lys Glu His Asp Gln Phe Ala Glu Thr Leu Lys Gln Gln
        50                  55                  60

Gly Ala Glu Val Leu Tyr Leu Glu Lys Leu Thr Ala Glu Ala Leu Asp
65              70                  75                  80

Asp Ala Leu Val Arg Glu Gln Phe Ile Asp Glu Leu Leu Thr Glu Ser
            85                  90                  95

Lys Ala Asp Ile Asn Gly Ala Tyr Asp Arg Leu Lys Glu Phe Leu Leu
            100                 105                 110

Thr Phe Asp Ala Asp Ser Met Val Glu Gln Val Met Ser Gly Ile Arg
        115                 120                 125

Lys Asn Glu Leu Glu Arg Glu Lys Lys Ser His Leu His Glu Leu Met
130                 135                 140

Glu Asp His Tyr Pro Phe Tyr Leu Asp Pro Met Pro Asn Leu Tyr Phe
145                 150                 155                 160

Thr Arg Asp Pro Ala Ala Ala Ile Gly Ser Gly Leu Thr Ile Asn Lys
            165                 170                 175

Met Lys Glu Pro Ala Arg Arg Arg Glu Ser Leu Phe Met Arg Tyr Ile
            180                 185                 190

Ile Asn His His Pro Arg Phe Lys Gly His Glu Ile Pro Val Trp Leu
```

```
                    195                 200                 205
Asp Arg Asp Phe Lys Phe Asn Ile Glu Gly Gly Asp Glu Leu Val Leu
    210                 215                 220

Asn Glu Glu Thr Val Ala Ile Gly Val Ser Glu Arg Thr Thr Ala Gln
225                 230                 235                 240

Ala Ile Glu Arg Leu Val Arg Asn Leu Phe Gln Arg Gln Ser Arg Ile
                245                 250                 255

Arg Arg Val Leu Ala Val Glu Ile Pro Lys Ser Arg Ala Phe Met His
            260                 265                 270

Leu Asp Thr Val Phe Thr Met Val Asp Arg Asp Gln Phe Thr Ile His
        275                 280                 285

Pro Ala Ile Gln Gly Pro Glu Gly Asp Met Arg Ile Phe Val Leu Glu
    290                 295                 300

Arg Gly Lys Thr Ala Asp Glu Ile His Thr Thr Glu His Asn Leu
305                 310                 315                 320

Pro Glu Val Leu Lys Arg Thr Leu Gly Leu Ser Asp Val Asn Leu Ile
                325                 330                 335

Phe Cys Gly Gly Asp Glu Ile Ala Ser Ala Arg Glu Gln Trp Asn
            340                 345                 350

Asp Gly Ser Asn Thr Leu Ala Ile Ala Pro Gly Val Val Thr Tyr
        355                 360                 365

Asp Arg Asn Tyr Ile Ser Asn Glu Cys Leu Arg Glu Gln Gly Ile Lys
    370                 375                 380

Val Ile Glu Ile Pro Ser Gly Glu Leu Ser Arg Gly Arg Gly Pro
385                 390                 395                 400

Arg Cys Met Ser Met Pro Leu Tyr Arg Glu Asp Val Lys
            405                 410

<210> SEQ ID NO 13
<211> LENGTH: 408
<212> TYPE: PRT
<213> ORGANISM: Enterococcus faecalis

<400> SEQUENCE: 13

Met Ser His Pro Ile Asn Val Phe Ser Glu Ile Gly Lys Leu Lys Thr
1               5                   10                  15

Val Met Leu His Arg Pro Gly Lys Glu Leu Glu Asn Leu Met Pro Asp
            20                  25                  30

Tyr Leu Glu Arg Leu Leu Phe Asp Asp Ile Pro Phe Leu Glu Lys Ala
        35                  40                  45

Gln Ala Glu His Asp Ala Phe Ala Glu Leu Leu Arg Ser Lys Asp Ile
    50                  55                  60

Glu Val Val Tyr Leu Glu Asp Leu Ala Ala Glu Ala Leu Ile Asn Glu
65                  70                  75                  80

Glu Val Arg Arg Gln Phe Ile Asp Gln Phe Leu Glu Glu Ala Asn Ile
                85                  90                  95

Arg Ser Glu Ser Ala Lys Glu Lys Val Arg Glu Leu Met Leu Glu Ile
            100                 105                 110

Asp Asp Asn Glu Glu Leu Ile Gln Lys Ala Ile Ala Gly Ile Gln Lys
        115                 120                 125

Gln Glu Leu Pro Lys Tyr Glu Gln Glu Phe Leu Thr Asp Met Val Glu
    130                 135                 140

Ala Asp Tyr Pro Phe Ile Ile Asp Pro Met Pro Asn Leu Tyr Phe Thr
145                 150                 155                 160
```

```
Arg Asp Asn Phe Ala Thr Met Gly His Gly Ile Ser Leu Asn His Met
            165                 170                 175

Tyr Ser Val Thr Arg Gln Arg Glu Thr Ile Phe Gly Gln Tyr Ile Phe
            180                 185                 190

Asp Tyr His Pro Arg Phe Ala Gly Lys Glu Val Pro Arg Val Tyr Asp
            195                 200                 205

Arg Ser Glu Ser Thr Arg Ile Glu Gly Gly Asp Glu Leu Ile Leu Ser
210                 215                 220

Lys Glu Val Val Ala Ile Gly Ile Ser Gln Arg Thr Asp Ala Ala Ser
225                 230                 235                 240

Ile Glu Lys Ile Ala Arg Asn Ile Phe Glu Gln Lys Leu Gly Phe Lys
            245                 250                 255

Asn Ile Leu Ala Phe Asp Ile Gly Glu His Arg Lys Phe Met His Leu
            260                 265                 270

Asp Thr Val Phe Thr Met Ile Asp Tyr Asp Lys Phe Thr Ile His Pro
            275                 280                 285

Glu Ile Glu Gly Gly Leu Val Val Tyr Ser Ile Thr Glu Lys Ala Asp
    290                 295                 300

Gly Asp Ile Gln Ile Thr Lys Glu Lys Asp Thr Leu Asp Asn Ile Leu
305                 310                 315                 320

Cys Lys Tyr Leu His Leu Asp Asn Val Gln Leu Ile Arg Cys Gly Ala
            325                 330                 335

Gly Asn Leu Thr Ala Ala Ala Arg Glu Gln Trp Asn Asp Gly Ser Asn
            340                 345                 350

Thr Leu Ala Ile Ala Pro Gly Glu Val Val Tyr Asp Arg Asn Thr
            355                 360                 365

Ile Thr Asn Lys Ala Leu Glu Glu Ala Gly Val Lys Leu Asn Tyr Ile
            370                 375                 380

Pro Gly Ser Glu Leu Val Arg Gly Arg Gly Pro Arg Cys Met Ser
385                 390                 395                 400

Met Pro Leu Tyr Arg Glu Asp Leu
            405

<210> SEQ ID NO 14
<211> LENGTH: 409
<212> TYPE: PRT
<213> ORGANISM: Lactobacillus sake

<400> SEQUENCE: 14

Met Thr Ser Pro Ile His Val Asn Ser Glu Ile Gly Lys Leu Lys Thr
1               5                   10                  15

Val Leu Leu Lys Arg Pro Gly Lys Glu Val Glu Asn Ile Thr Pro Asp
            20                  25                  30

Ile Met Tyr Arg Leu Leu Phe Asp Asp Ile Pro Tyr Leu Pro Thr Ile
            35                  40                  45

Gln Lys Glu His Asp Gln Phe Ala Gln Thr Leu Arg Asp Asn Gly Val
    50                  55                  60

Glu Val Leu Tyr Leu Glu Asn Leu Ala Ala Glu Ala Ile Asp Ala Gly
65                  70                  75                  80

Asp Val Lys Glu Ala Phe Leu Asp Lys Met Leu Asn Glu Ser His Ile
            85                  90                  95

Lys Ser Pro Gln Val Gln Ala Ala Leu Lys Asp Tyr Leu Ile Ser Met
            100                 105                 110

Ala Thr Leu Asp Met Val Glu Lys Ile Met Ala Gly Val Arg Thr Asn
            115                 120                 125
```

```
-continued

Glu Ile Asp Ile Lys Ser Lys Ala Leu Ile Asp Val Ser Ala Asp Asp
    130             135                 140

Asp Tyr Pro Phe Tyr Met Asp Pro Met Pro Asn Leu Tyr Phe Thr Arg
145             150                 155                 160

Asp Pro Ala Ala Ser Met Gly Asp Gly Leu Thr Ile Asn Lys Met Thr
                165                 170                 175

Phe Glu Ala Arg Gln Arg Glu Ser Met Phe Met Glu Val Ile Met Gln
            180                 185                 190

His His Pro Arg Phe Ala Asn Gln Gly Ala Gln Val Trp Arg Asp Arg
        195                 200                 205

Asp His Ile Asp Arg Met Glu Gly Gly Asp Glu Leu Ile Leu Ser Asp
    210                 215                 220

Lys Val Leu Ala Ile Gly Ile Ser Gln Arg Thr Ser Ala Gln Ser Ile
225                 230                 235                 240

Glu Glu Leu Ala Lys Val Leu Phe Ala Asn His Ser Gly Phe Glu Lys
                245                 250                 255

Ile Leu Ala Ile Lys Ile Pro His Lys His Ala Met Met His Leu Asp
            260                 265                 270

Thr Val Phe Thr Met Ile Asp Tyr Asp Lys Phe Thr Ile His Pro Gly
        275                 280                 285

Ile Gln Gly Ala Gly Gly Met Val Asp Thr Tyr Ile Leu Glu Pro Gly
    290                 295                 300

Asn Asn Asp Glu Ile Lys Ile Thr His Gln Thr Asp Leu Glu Lys Val
305                 310                 315                 320

Leu Arg Asp Ala Leu Glu Val Pro Glu Leu Thr Leu Ile Pro Cys Gly
                325                 330                 335

Gly Gly Asp Ala Val Val Ala Pro Arg Glu Gln Trp Asn Asp Gly Ser
            340                 345                 350

Asn Thr Leu Ala Ile Ala Pro Gly Val Val Val Thr Tyr Asp Arg Asn
        355                 360                 365

Tyr Val Ser Asn Glu Asn Leu Arg Gln Tyr Gly Ile Lys Val Ile Glu
    370                 375                 380

Val Pro Ser Ser Glu Leu Ser Arg Gly Arg Gly Gly Pro Arg Cys Met
385                 390                 395                 400

Ser Met Pro Leu Val Arg Arg Lys Thr
                405
```

METHOD OF TREATMENT WITH MODIFIED ARGININE DEIMINASE

CROSS REFERENCE TO RELATED APPLICATIONS

This application is a divisional of U.S. patent application Ser. No. 09/723,546, filed Nov. 28, 2000, now U.S. Pat. No. 6,737,259, which is a continuation-in-part of U.S. patent application Ser. No. 09/023,809, filed Feb. 13, 1998, now U.S. Pat. No. 6,183,738, which claims the benefit of U.S. Provisional Application Ser. No. 60/046,200, filed May 12, 1997, each of which is incorporated herein by reference.

FIELD OF THE INVENTION

The present invention is directed to arginine deiminase modified with polyethylene glycol, to methods for treating cancer, and to methods for treating and/or inhibiting metastasis.

BACKGROUND OF THE INVENTION

Malignant melanoma (stage 3) and hepatoma are fatal diseases which kill most patients within one year of diagnosis. In the United States, approximately 16,000 people die from these diseases annually. The incidence of melanoma is rapidly increasing in the United States and is even higher in other countries, such as Australia. The incidence of hepatoma, in parts of the world where hepatitis is endemic, is even greater. For example, hepatoma is one of the leading forms of cancer in Japan and Taiwan. Effective treatments for these diseases are urgently needed.

Selective deprivation of essential amino acids has been used to treat some forms of cancer. The best known example is the use of L-asparaginase to lower levels of asparagine as a treatment for acute lymphoblastic leukemia. The L-asparaginase most frequently used is isolated from *E. coli*. However, clinical use of this enzyme is compromised by its inherent antigenicity and short circulating half-life, as described by Y. K. Park, et al, *Anticancer Res.*, 1:373-376 (1981). Covalent modification of *E. coli* L-asparaginase with polyethylene glycol reduces its antigenicity and prolongs its circulating half-life, as described, for example, by Park, *Anticancer Res.*, supra; Y. Kamisaki et al, *J. Pharmacol. Exp. Ther.*, 216:410-414 (1981); and Y. Kamisaki et al, *Gann.*, 73:47-474 (1982). Although there has been a great deal of effort to identify other essential amino acid degrading enzymes for the treatment of cancer, none have been approved, primarily because deprivation of essential amino acids, by definition, results in numerous, and severe, side effects.

It has been reported that enzymes which degrade non-essential amino acids, such as arginine, may be an effective means of controlling some forms of cancer. For example, arginine deiminase (ADI) isolated from *Pseudomonas pudita* was described by J. B. Jones, "The Effect of Arginine Deiminase on Murine Leukemic Lymphoblasts," Ph.D. Dissertation, The University of Oklahoma, pages 1-165 (1981). Although effective in killing tumor cells in vitro, ADI isolated from *P. pudita* failed to exhibit efficacy in vivo because it had little enzyme activity at a neutral pH and was rapidly cleared from the circulation of experimental animals. Arginine deiminase derived from *Mycoplasma arginini* is described, for example, by Takaku et al, *Int. J. Cancer*, 51:244-249 (1992), and U.S. Pat. No. 5,474,928, the disclosures of which are hereby incorporated by reference herein in their entirety. However, a problem associated with the therapeutic use of such a heterologous protein is its antigenicity. The chemical modification of arginine deiminase from *Mycoplasma arginini*, via a cyanuric chloride linking group, with polyethylene glycol was described by Takaku et al., *Jpn. J. Cancer Res.*, 84:1195-1200 (1993). However, the modified protein was toxic when metabolized due to the release of cyanide from the cyanuric chloride linking group.

There is a need for compositions which degrade non-essential amino acids and which do not have the problems associated with the prior art. The present invention is directed to these, as well as other, important ends.

SUMMARY OF THE INVENTION

The present invention is directed to arginine deiminase modified with polyethylene glycol. In a preferred embodiment, the arginine deiminase is modified with polyethylene glycol, having a total weight average molecular weight of about 1,000 to about 50,000, directly or through a biocompatible linking group.

Another embodiment of the invention is directed to methods of treating cancer, including, for example, sarcomas, hepatomas and melanomas. The invention is also directed to methods of treating and/or inhibiting the metastasis of tumor cells.

These and other aspects of the present invention will be elucidated in the following detailed description of the invention.

BRIEF DESCRIPTION OF THE DRAWINGS

FIG. 1 depicts the amino acid sequences of arginine deiminase cloned from *Mycoplasma arginini* (the top amino acid sequence SEQ ID NO: 1, identified as ADIPROT), *Mycoplasma arthritides* (the middle amino acid sequence SEQ ID NO: 2, identified as ARTADIPRO), and *Mycoplasma hominus* (the bottom amino acid sequence SEQ ID NO: 3, identified as HOMADIPRO).

FIGS. 2A and 2B are graphs showing the effect of a single dose of native arginine deiminase and arginine deiminase modified with polyethylene glycol (e.g., molecular weight 5,000) on serum arginine levels and serum citrulline levels in mice.

FIG. 3 is a graph showing the effects on serum arginine levels when PEG10,000 is covalently bonded to ADI via various linking groups.

FIG. 4 is a graph showing the effect that the linking group and the molecular weight of the polyethylene glycol have on citrulline production in mice injected with a single dose of PEG-ADI.

FIGS. 5A and 5B are graphs showing the dose response that ADI-SS-PEG5,000 had on serum arginine and citrulline levels.

FIGS. 5C and 5D are graphs showing the dose response that ADI-SS-PEG20,000 had on serum arginine and citrulline levels.

FIG. 10 depicts the amino acid sequences of arginine deiminase cloned from *Steptococcus pyogenes* (the top amino acid sequence SEQ ID NO: 6, identified as STRADIPYR) and *Steptococcus pneumoniae* (the bottom amino acid sequence SEQ ID NO: 7, identified as STRADIPNE).

FIG. 11 depicts the amino acid sequences of arginine deiminase cloned from *Borrelia burgdorferi* (the top amino acid sequence SEQ ID NO: 8, identified as BORADIBUR) and *Borrelia afzelii* (the bottom amino acid sequence SEQ ID NO: 9, identified as BORADIAFZ).

FIG. 12 depicts the amino acid sequence of *Qiardia intestinalis* (the top amino acid sequence SEQ ID NO: 10, identified as QIAADIINT), *Clostridium perfringens* (the middle amino acid sequence SEQ ID NO: 11, identified as CLOADIPER) and *Bacillus licheniformis* (the bottom amino acid sequence SEQ ID NO: 12, identified as BACADILIC).

FIG. 13 depicts the amino acid sequence of *Enterococcus faecalis* (the top amino acid sequence SEQ ID NO: 13, identified as ENTADIFAE) and *Lactobacillus sake* (the bottom amino acid sequence SEQ ID NO: 14, identified as LACADISAK).

DETAILED DESCRIPTION OF THE INVENTION

Figure 6:
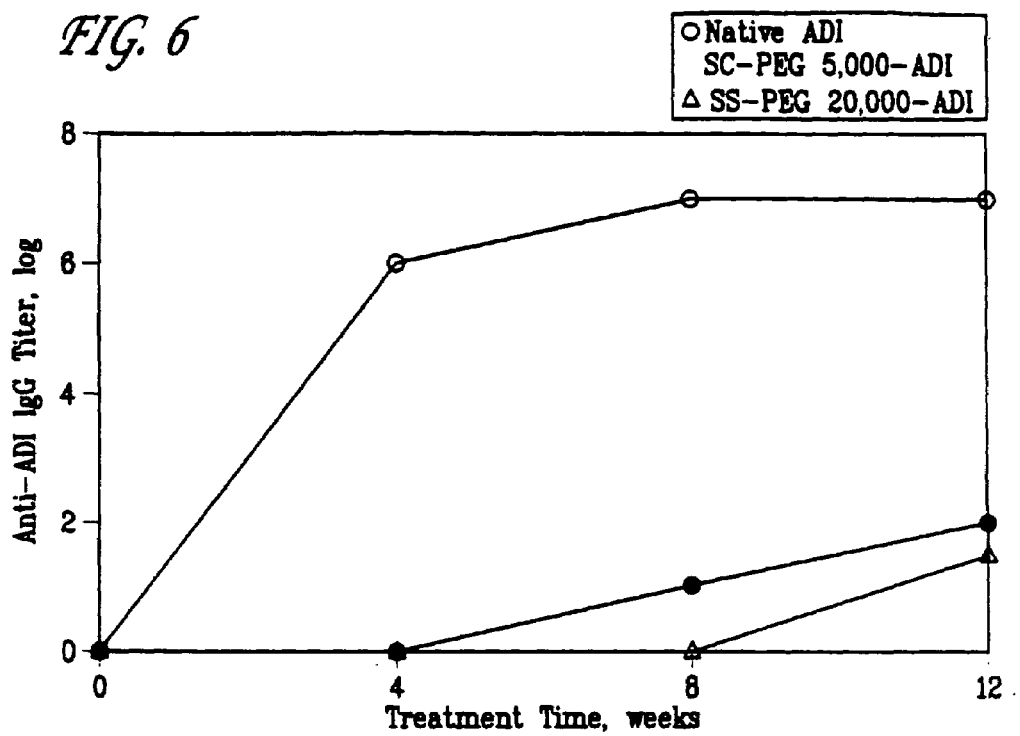
FIG. 6 is a graph showing the antigenicity of native ADI, ADI-SS-PEG5,000, and ADI-SS-PEG20,000.

Normal cells do not require arginine for growth, since they can synthesize arginine from citrulline in a two step process catalyzed by argininosuccinate synthase and argininosuccinate lyase. In contrast, melanomas, hepatomas and some sarcomas do not express arginosuccinate synthase; therefore, they are auxotrophic for arginine. This metabolic difference may be capitalized upon to develop a safe and effective therapy to treat these forms of cancer. Arginine deiminase catalyzes the conversion of arginine to citrulline, and may be used to eliminate arginine. Thus, arginine deiminase may be utilized as a treatment for melanomas, hepatomas and some sarcomas.

Native arginine deiminase may be found in microorganisms and is antigenic and rapidly cleared from circulation in a patient. These problems may be overcome by covalently modifying arginine deiminase with polyethylene glycol (PEG). Arginine deiminase covalently modified with polyethylene glycol (with or without a linking group) may be hereinafter referred to as "ADI-PEG." When compared to native arginine deiminase, ADI-PEG retains most of its enzymatic activity, is far less antigenic, has a greatly extended circulating half-life, and is much more efficacious in the treatment of tumors.

"Polyethylene glycol" or "PEG" refers to mixtures of condensation polymers of ethylene oxide and water, in a branched or straight chain, represented by the general formula $H(OCH_2CH_2)_nOH$, wherein n is at least 4. "Polyethylene glycol" or "PEG" is used in combination with a numeric suffix to indicate the approximate weight average molecular weight thereof. For example, PEG5,000 refers to polyethylene glycol having a total weight average molecular weight of about 5,000; PEG12,000 refers to polyethylene glycol having a total weight average molecular weight of about 12,000; and PEG20,000 refers to polyethylene glycol having a total weight average molecular weight of about 20,000.

"Melanoma" may be a malignant or benign tumor arising from the melanocytic system of the skin and other organs, including the oral cavity, esophagus, anal canal, vagina, leptomeninges, and/or the conjunctivae or eye. The term "melanoma" includes, for example, acral-lentiginous melanoma, amelanotic melanoma, benign juvenile melanoma, lentigo maligna melanoma, malignant melanoma, nodular melanoma, subungual melanoma and superficial spreading melanoma.

"Hepatoma" may be a malignant or benign tumor of the liver, including, for example, hepatocellular carcinoma.

"Patient" refers to an animal, preferably a mammal, more preferably a human.

"Biocompatible" refers to materials or compounds which are generally not injurious to biological functions and which will not result in any degree of unacceptable toxicity, including allergenic and disease states.

Throughout the present disclosure, the following abbreviations may be used: PEG, polyethylene glycol; ADI, arginine deiminase; SS, succinimidyl succinate; SSA, succinimidyl succinamide; SPA, succinimidyl propionate; and NHS, N-hydroxy-succinimide.

The present invention is based on the unexpected discovery that ADI modified with polyethylene glycol provides excellent results in treating certain types of cancer and inhibiting the metastasis of cancer. ADI may be covalently bonded to polyethylene glycol with or without a linking group, although a preferred embodiment utilizes a linking group.

In the present invention, the arginine deiminase gene may be derived, cloned or produced from any source, including, for example, microorganisms, recombinant biotechnology or any combination thereof. For example, arginine deiminase may be cloned from microorganisms of the genera *Mycoplasma, Clostridium, Bacillus, Borrelia, Enterococcus, Streptococcus, Lactobacillus, Qiardia*. It is preferred that arginine deiminase is cloned from *Mycoplasma pneumoniae, Mycoplasma hominus, Mycoplasma arginini, Steptococcus pyogenes, Steptococcus pneumoniae, Borrelia burgdorferi, Borrelia afzelii, Qiardia intestinalis, Clostridium perfringens, Bacillus licheniformis, Enterococcus faecalis, Lactobacillus sake*, or any combination thereof. In particular, the arginine deiminase used in the present invention may have one or more of the amino acid sequences depicted in FIGS. 1 and 10-13.

In certain embodiments of the present invention, it is preferred that arginine deiminase is cloned from microorganisms of the genus *Mycoplasma*. More preferably, the arginine deiminase is cloned from *Mycoplasma arginini, Mycoplasma hominus, Mycoplasma arthritides*, or any combination thereof. In particular, the arginine deiminase used in the present invention may have one or more of the amino acid sequences depicted in FIG. 1.

In one embodiment of the present invention, the polyethylene glycol (PEG) has a total weight average molecular weight of about 1,000 to about 50,000; more preferably from about 3,000 to about 40,000, more preferably from about 5,000 to about 30,000; more preferably from about 8,000 to about 30,000; more preferably from about 11,000 to about 30,000; even more preferably from about 12,000 to about 28,000; still more preferably from about 16,000 to about 24,000; even more preferably from about 18,000 to about 22,000; even more preferably from about 19,000 to about 21,000, and most preferably about 20,000. Generally, polyethylene glycol with a molecular weight of 30,000 or more is-difficult to dissolve, and yields of the formulated product are greatly reduced. The polyethylene glycol may be a branched or straight chain, preferably a straight chain. Generally, increasing the molecular weight of the polyethylene glycol decreases the immunogenicity of the ADI. The polyethylene glycol having a molecular weight described in this embodiment may be used in conjunction with ADI, and, optionally, a biocompatible linking group, to treat cancer, including, for example, melanomas, hepatomas and sarcomas, preferably melanomas.

In another embodiment of the present invention, the polyethylene glycol has a total weight average molecular weight of about 1,000 to about 50,000; preferably about 3,000 to about 30,000; more preferably from about 3,000 to about 20,000; more preferably from about 4,000 to about 12,000; still more preferably from about 4,000 to about 10,000; even more preferably from about 4,000 to about 8,000; still more preferably from about 4,000 to about 6,000; with about 5,000 being most preferred. The polyethylene glycol may be a branched or straight chain, preferably a straight chain. The polyethylene glycol having a molecular weight described in this embodiment may be used in conjunction with ADI, and optionally, a biocompatible linking group, to treat cancer, including, for example, melanomas, hepatomas and sarcomas, preferably hepatomas.

The linking group used to covalently attach ADI to PEG may be any biocompatible linking group. As discussed above, "biocompatible" indicates that the compound or group is non-toxic and may be utilized in vitro or in vivo without causing injury, sickness, disease or death. PEG can be bonded to the linking group, for example, via an ether bond, an ester bond, a thiol bond or an amide bond. Suitable biocompatible linking groups include, for example, an ester group, an amide group, an imide group, a carbamate group, a carboxyl group, a hydroxyl group, a carbohydrate, a succinimide group (including, for example, succinimidyl succinate (SS), succinimidyl propionate (SPA), succinimidyl carboxymethylate (SCM), succinimidyl succinamide (SSA) or N-hydroxy succinimide (NHS)), an epoxide group, an oxycarbonylimidazole group (including, for example, carbonyldimidazole (CDI)), a nitro phenyl group (including, for example, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine. Preferably, the biocompatible linking group is an ester group and/or a succinimide group. More preferably, the linking group is SS, SPA, SCM, SSA or NHS; with SS, SPA or NHS being more preferred, and with SS or SPA being most preferred.

Alternatively, ADI may be coupled directly to PEG (i.e., without a linking group) through an amino group, a sulfhydral group, a hydroxyl group or a carboxyl group.

ADI may be covalently bonded to PEG, via a biocompatible linking group, using methods known in the art, as described, for example, by Park et al, *Anticancer Res.*, 1:373-376 (1981); and Zaplipsky and Lee, *Polyethylene Glycol Chemistry: Biotechnical and Biomedical Applications*, J. M. Harris, ed., Plenum Press, NY, Chapter 21 (1992), the disclosures of which are hereby incorporated by reference herein in their entirety.

The attachment of PEG to ADI increases the circulating half-life of ADI. Generally, PEG is attached to a primary amine of ADI. Selection of the attachment site of polyethylene glycol on the arginine deiminase is determined by the role of each of the sites within the active domain of the protein, as would be known to the skilled artisan. PEG may be attached to the primary amines of arginine deiminase without substantial loss of enzymatic activity. For example, ADI cloned from *Mycoplasma arginini, Mycoplasma arthritides* and *Mycoplasma hominus* has about 17 lysines that may be modified by this procedure. In other words, the 17 lysines are all possible points at which ADI can be attached to PEG via a biocompatible linking group, such as SS, SPA, SCM, SSA and/or NHS. PEG may also be attached to other sites on ADI, as would be apparent to one skilled in the art in view of the present disclosure.

From 1 to about 30 PEG molecules may be covalently bonded to ADI. Preferably, ADI is modified with about 7 to about 15 PEG molecules, more preferably from about 9 to about 12 PEG molecules. In other words, about 30% to about 70% of the primary amino groups in arginine deiminase are modified with PEG, preferably about 40% to about 60%, more preferably about 45% to about 55%, and most preferably about 50% of the primary amino groups in arginine deiminase are modified with PEG. When PEG is covalently bonded to the end terminus of ADI, preferably only 1 PEG molecule is utilized. Increasing the number of PEG units on ADI increases the circulating half life of the enzyme. However, increasing the number of PEG units on ADI decreases the specific activity of the enzyme. Thus, a balance needs to be achieved between the two, as would be apparent to one skilled in the art in view of the present disclosure.

In the present invention, a common feature of the most preferred biocompatible linking groups is that they attach to a primary amine of arginine deiminase via a maleimide group. Once coupled with arginine deiminase, SS-PEG has an ester linkage next to the PEG, which may render this site sensitive to serum esterase, which may release PEG from ADI in the body. SPA-PEG and PEG2-NHS do not have an ester linkage, so they are not sensitive to serum esterase.

In the present invention, the particular linking groups do not appear to influence the circulating half-life of PEG-ADI or its specific enzyme activity. However, it is critical to use a biocompatible linking group in the present invention. PEG which is attached to the protein may be either a single chain, as with SS-PEG, SPA-PEG and SC-PEG, or a branched chain of PEG may be used, as with PEG2-NHS. The structural formulas of the preferred linking groups in the present invention are set forth below.

SS-PEG:

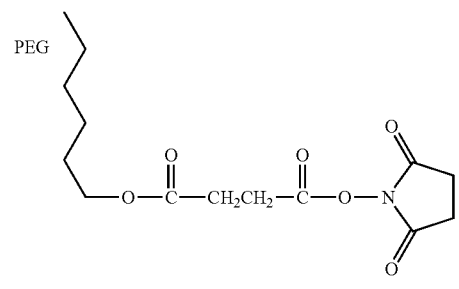

SS

SPA-PEG:

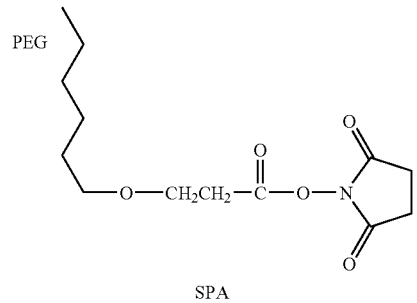

SPA

-continued

PEG2-NHS:

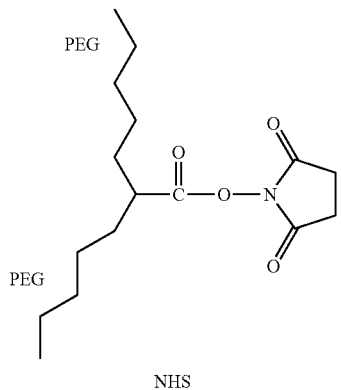

A therapeutically effective amount of one of the compounds of the present invention is an amount that is effective to inhibit tumor growth. Generally, treatment is initiated with small dosages which can be increased by small increments until the optimum effect under the circumstances is achieved. Generally, a therapeutic dosage of compounds of the present invention may be from about 1 to about 200 mg/kg twice a week to about once every two weeks. For example, the dosage may be about 1 mg/kg once a week as a 2 ml intravenous injection to about 20 mg/kg once every 3 days. The optimum dosage with ADI-SS-PEG5,000 may be about twice a week, while the optimum dosage with ADI-SS-PEG20,000 may be from about once a week to about once every two weeks. PEG-ADI may be mixed with a phosphate buffered saline solution, or any other appropriate solution known to those skilled in the art, prior to injection. The PEG-ADI formulation may be administered as a solid (lyophilate) or as a liquid formulation, as desired.

The methods of the present invention can involve either in vitro or in vivo applications. In the case of in vitro applications, including cell culture applications, the compounds described herein can be added to the cells in cultures and then incubated. The compounds of the present invention may also be used to facilitate the production of monoclonal and/or polyclonal antibodies, using antibody production techniques well known in the art. The monoclonal and/or polyclonal antibodies can then be used in a wide variety of diagnostic applications, as would be apparent to one skilled in the art.

The in vivo means of administration of the compounds of the present invention will vary depending upon the intended application. As one skilled in the art will recognize, administration of the PEG-ADI composition of the present invention can be carried out, for example, orally, intranasally, intraperitoneally, parenterally, intravenously, intralymphatically, intratumorly, intramuscularly, interstitially, intra-arterially, subcutaneously, intraocularly, intrasynovial, transepithelial, and transdermally.

EXAMPLES

The invention is further demonstrated in the following examples, which are for purposes of illustration, and are not intended to limit the scope of the present invention.

Example 1

Production of Recombinant ADI

Cultures of *Mycoplasma arginini* (ATCC 23243), *Mycoplasma hominus* (ATCC 23114) and *Mycoplasma arthritides* (ATCC 23192) were obtained from the American Type Culture Collection, Rockville, Md.

Arginine deiminase was cloned from *Mycoplasma arginini, Mycoplasma hominus* and *Mycoplasma arthritides* and expressed in *E. coli* as previously described by S. Misawa et al, *J. Biotechnology*, 36:145-155 (1994), the disclosure of which is hereby incorporated herein by reference in its entirety. The amino acid sequences of arginine deiminase from each of the above species is set forth in FIG. 1. The top amino acid sequence, identified as ADIPROT, is from *Mycoplasma arginini*; the middle amino acid sequence, identified as ARTADIPRO, is from *Mycoplasma arthritides*; and the bottom amino acid sequence, identified as HOMADIPRO, is from *Mycoplasma hominus*. Each of the amino acid sequences are more than 96% conserved. Characterization, by methods known to those skilled in the art, of each of the proteins with respect to specific enzyme activity, $K_m$, $V_{max}$ and pH optima revealed that they were biochemically indistinguishable from each other. The pH optima was determined using a citrate buffer (pH 5-6.5), a phosphate buffer (pH 6.5-7.5) and a borate buffer (pH 7.5-8.5). The $K_m$ and $V_{max}$ were determined by incubating the enzyme with various concentrations of arginine and quantifying citrulline production. The $K_m$ for the various enzymes was about 0.02 to 0.06 µM and the $V_{max}$ was about 15-20 µmol/min/mg, the values of which are within standard error of each other.

The arginine deiminase genes were amplified by polymerase chain reaction using the following primer pair derived from the published sequence of *M. arginini*, as described, for example, by T. Ohno et al, *Infect. Immun.*, 58:3788-3795 (1990), the disclosure of which is hereby incorporated by reference herein in its entirety:

```
                                      SEQ ID NO: 4
5'-GGGATCCATGTCTGTATTTGACAGT-3',

SEQ ID NO: 5
5'-TGAAAGCTTTTACTACCACTTAACATCTTTACG-3',
```

The polymerase chain reaction products were cloned as a Bam HI-Hind III fragment into expression plasmid pQE16. DNA sequence analysis indicated that the fragment derived from *M. arginini* by PCR had the same sequence for the arginine deiminase gene as described by Ohno et al, *Infect. Immun.*, supra. The five TGA codons in the ADI gene which encode tryptophan in *Mycoplasma* were changed to TGG codons by oligonucleotide-directed mutagenesis prior to gene expression in *E. coli*, as taught, for example, by J. R. Sayers et al, *Biotechniques*, 13:592-596 (1992). Recombinant ADI was expressed in inclusion bodies at levels of 10% of total cell protein.

The proteins from each of the above three species of *Mycoplasma* have approximately 95% homology and are readily purified by column chromatography. Approximately 200 mg of pure protein may be isolated from 1 liter of fermentation broth. Recombinant ADI is stable for about 2 weeks at 37° C. and for at least 8 months when stored at 4° C. As determined by methods known to those skilled in the art, the proteins had a high affinity for arginine (0.04 µM), and a physiological pH optima of about 7.2 to about 7.4.

Example 2

Renaturation and Purification of Recombinant ADI

ADI protein was renatured, with minor modifications, as described by Misawa et al, *J. Biotechnology*, 36:145-155 (1994), the disclosure of which is hereby incorporated herein by reference in its entirety. 100 g of cell paste was resuspended in 800 ml of 10 mM $K_2PO_4$ pH 7.0, 1 mM EDTA (buffer 1) and the cells were disrupted by two passes in a Microfluidizer (Microfluidics Corporation, Newton, Mass.). Triton X-100 was added to achieve a final concentration of 4% (v/v). The homogenate was stirred for 30 min at 4° C., then centrifuged for 30 min at 13,000 g. The pellet was collected and resuspended in one liter of buffer 1 containing 0.5% Triton X-100. The solution was diafiltered against 5 volumes of denaturation buffer (50 mM Tris HCl, pH 8.5, 10 mM DTT) using hollow-fiber cartridges with 100 kD retention rating (Microgon Inc., Laguna Hills, Calif.). Guanidine HCl was added to achieve a final concentration of 6 M and the solution was stirred for 15 min at 4° C. The solution was diluted 100-fold into refolding buffer 1, 10 mm $K_2PO_4$, pH 7.0 and stirred for 48 hours at 15° C., particulates were removed by centrifugation at 15,000×g.

The resulting supernatant was concentrated on a Q Sepharose Fast Flow (Pharmacia Inc., Piscataway, N.J.) column preequilabrated in refolding buffer. ADI was eluted using refolding buffer containing 0.2 M NaCl. The purification procedure yielded ADI protein, which was >95% pure as estimated by SDS-PAGE analysis. 8 g of pure renatured ADI protein was produced from 1 kg of cell paste which corresponds to 200 mg purified ADI per liter of fermentation.

ADI activity was determined by micro-modification of the method described by Oginsky et al, *Meth. Enzymol.*, (1957) 3:639-642. 10 µl samples in 0.1 m $Na_2PO_4$, pH 7.0 (BUN assay buffer) were placed in a 96 well microliter plate, 40 µl of 0.5 mM arginine in BUN assay buffer was added, and the plate was covered and incubated at 37° C. for 15 minutes. 20 µl of complete BUN reagent (Sigma Diagnostics) was added and the plate was incubated for 10 minutes at 100° C. The plate was then cooled to 22° C. and analyzed at 490 nm by a microliter plate reader (Molecular Devices, Inc). 1.0 IU is the amount of enzyme which converts 1 µmole of L-arginine to L-citrulline per minute. Protein concentrations were determined using Pierce Coomassie Blue Protein Assay Reagent (Pierce Co., Rockford, Ill.) with bovine serum albumin as a standard.

The enzyme activity of the purified ADI preparations was 17-25 IU/mg.

Example 3

Attachment of PEG to ADI

PEG was covalently bonded to ADI in a 100 mM phosphate buffer, pH 7.4. Briefly, ADI in phosphate buffer was mixed with a 100 molar excess of PEG. The reaction was stirred at room temperature for 1 hour, then the mixture was extensively dialized to remove unincorporated PEG.

A first experiment was performed where the effect of the linking group used in the PEG-ADI compositions was evaluated. PEG and ADI were covalently bonded via four different linking groups: an ester group or maleimide group, including SS, SSA, SPA and SSPA, where the PEG had a total weight average molecular weight of 5,000, 10,000, 12,000, 20,000, 30,000 and 40,000; an epoxy group, PEG-epoxy, where the PEG had a total weight average molecular weight of 5,000; and a branched PEG group, PEG2-NHS, where the PEG had a total weight average molecular weight of 10,000, 20,000 and 40,000.

5.0 IU of the resulting compositions were injected into mice (5 mice in each group). To determine the serum levels of arginine, the mice were bled from the retro orbital plexus (100 ul). Immediately following collection an equal volume of 50% (w/v) of trichloroacetic acid was added. The precipitate was removed by centrifugation (13,000×g for 30 minutes) and the supernatant removed and stored frozen at −70° C. The samples were then analyzed using an automated amino acid analyzer and reagents from Beckman Instruments using protocols supplied by the manufacturer. The limits of sensitivity for arginine by this method was approximately 2-6 µM and the reproducibility of measurements within about 8%. The amount of serum arginine was determined by amino acid analysis. As can be seen from the results in FIG. 3, the linking group covalently bonding the PEG and ADI did not have an appreciable effect on the ability of ADI to reduce serum arginine in vivo. In other words, the linking group may not be critical to the results of the experiment, except that a non-toxic linking group must be used for in vivo applications.

A second experiment was performed wherein the effect of the linking group and molecular weight of PEG on serum citrulline levels in vivo was evaluated. Mice (5 in each group) were given various compositions of ADI and PEG-ADI in an amount of 5.0 IU. To determine the serum levels of citrulline, the mice were bled from the retro orbital plexus (100 ul). Immediately following collection an equal volume of 50% (w/v) of trichloroacetic acid was added. The precipitate was removed by centrifugation (13,000×g for 30 minutes) and the supernatant removed and stored frozen at −70° C. The samples were then analyzed using an automated amino acid analyzer and reagents from Beckman Instruments using protocols supplied by the manufacturer. The limits of sensitivity for citrulline by this method was approximately 2-6 µM and the reproducibility of measurements within about 8%. The amount of citrulline was determined, and the area under the curve approximated and expressed as µmol days.

In FIG. 4, the open circles indicate the amount of citrulline produced by native ADI, the filled circles are ADI-SC-PEG, the open squares are ADI-SS-PEG, the open triangles are ADI-SPA-PEG, and the filled triangles are branched chain PEG-NHS-$PEG_2$. The results in FIG. 4 demonstrate that the molecular weight of the PEG determines the effectiveness of the PEG-ADI composition. The effectiveness of the PEG-ADI compositions is not necessarily based on the method or means of attachment of the PEG to ADI, except that a biocompatible linking group must be used for in vivo applications.

The results in FIG. 4 also demonstrate that the optimal molecular weight of PEG is 20,000. Although PEG30,000 appears to be superior to PEG20,000 in terms of its pharmacodynamics, PEG30,000 is less soluble, which makes it more difficult to work with. The yields, which were based on the recovery of enzyme activity, were about 90% for PEG5,000 and PEG12,000; about 85% for PEG20,000 and about 40% for PEG30,000. Therefore, PEG20,000 is the best compromise between yield and circulating half life, as determined by citrulline production.

In a third experiment, the dose response of serum arginine depletion and the production of citrulline with ADI-SS-PEG5,000 and ADI-SS-PEG20,000 was determined. Mice (5 in each group) were given a single injection of 0.05 IU, 0.5 IU or 5.0 IU of either ADI-SS-PEG5,000 or ADI-SS-PEG20,000. At indicated times, serum was collected, as described above, and an amino acid analysis was performed to quantify serum arginine (FIGS. 5A and 5C) and serum citrulline (FIGS. 5B and 5D). Both formulations induced a dose dependent decrease in serum arginine and an increase in serum citrulline. However, the effects induced by ADI-SS-PEG20,000 were more pronounced and of longer duration than the effects induced by ADI-SS-PEG5,000.

Example 4

Selectivity of ADI Mediated Cytotoxicity

The selectivity of arginine deiminase mediated cytotoxicity was demonstrated using a number of human tumors. Specifically, human tumors were tested in vitro for sensitivity to ADI-SS-PEG5,000 (50 ng/ml). Viability of cultures was determined after 7 days. For a culture to be defined as "inhibited," greater than 95% of the cells must take up Trypan blue dye. A host of normal cells were also tested, including endothelial cells, smooth muscle cells, epithelial cells and fibroblasts, and none were inhibited by ADI-SS-PEG5,000. Although arginine deiminase has no appreciable toxicity towards normal, and most tumor cells, ADI-SS-PEG5,000 greatly inhibited all human melanomas and hepatomas that were commercially available from the ATCC, MSKCC and Europe.

TABLE 1

Specificity of Arginine Deiminase Cytotoxicity

| Tumor Type | Number of Tumors Tested | Tumors inhibited (%) |
|---|---|---|
| Brain | 16 | 0 |
| Colon | 34 | 0 |
| Bladder | 3 | 0 |
| Breast | 12 | 0 |
| Kidney | 5 | 0 |
| Sarcoma | 11 | 64 |
| Hepatoma | 17 | 100 |
| Melanoma | 37 | 100 |

In a parallel set of experiments, mRNA was isolated from the tumors. Northern blot analyses, using the human argininosuccinate synthase cDNA probe, indicated complete concordance between the sensitivity to arginine deiminase treatment and an inability to express argininosuccinate synthase. This data suggests that ADI toxicity results from an inability to induce argininosuccinate synthase. Therefore, these cells cannot synthesize arginine from citrulline, and are unable to synthesize the proteins necessary for growth.

Example 5

Circulating Half-Life

Balb C mice (5 in each group) were injected intravenously with a single 5.0 IU dose of either native arginine deiminase or various formulations of arginine deiminase modified with polyethylene glycol, as indicated in FIGS. 2A and 2B. To determine the serum levels of arginine and citrulline, the mice were bled from the retro orbital plexus (100 µl). Immediately following collection an equal volume of 50% (w/v) of trichloro-acetic acid was added. The precipitate was removed by centrifugation (13,000×g for 30 minutes) and the supernatant removed and stored frozen at −70° C. The samples were then analyzed using an automated amino acid analyzer and reagents from Beckman Instruments using protocols supplied by the manufacturer. The limits of sensitivity for arginine by this method was approximately 6 µM and the reproducibility of measurements within about 8%.

A dose dependent decrease in serum arginine levels, as shown by the solid circles in FIG. 2A, and a rise in serum citrulline, as shown by the open triangles in FIG. 2B, were detected from the single dose administration of native ADI (filled circles) or ADI-SS-PEG (open triangles). However, the decrease in serum arginine and rise in serum citrulline was short lived, and soon returned to normal. The half life of arginine depletion is summarized in the Table below.

TABLE 2

Half-Life of Serum Arginine Depletion

| Compound | Half-Life in Days |
|---|---|
| Native ADI | 1 |
| ADI-SS-PEG5,000 | 5 |
| ADI-SS-PEG12,000 | 15 |
| ADI-SS-PEG20,000 | 20 |
| ADI-SS-PEG30,000 | 22 |

This experiment demonstrates that normal cells and tissues are able to convert the citrulline back into arginine intracellularly while melanomas and hepatomas cannot because they lack argininosuccinate synthetase.

Example 6

Antigenicity of PEG Modified ADI

To determine the antigenicity of native ADI, ADI-SS-PEG5,000, and ADI-SS-PEG20,000, the procedures described in, for example, Park, *Anticancer Res.*, supra, and Kamisaki, *J. Pharmacol. Exp. Ther.*, supra, were followed. Briefly, Balb C mice (5 in each group) were intravenously injected weekly for 12 weeks with approximately 0.5 IU (100 µg of protein) of native ADI, ADI-SS-PEG5,000 or ADI-SS-PEG20,000. The animals were bled (0.05 ml) from the retro orbital plexus at the beginning of the experiment and at weeks 4, 8 and 12. The serum was isolated and stored at −70° C. The titers of anti-ADI IgG were determined by ELISA. 50 µg of ADI was added to each well of a 96 well micro-titer plate and was incubated at room temperature for 4 hours. The plates were rinsed with PBS and then coated with bovine serum albumin (1 mg/ml) to block nonspecific protein binding sites, and stored over night at 4° C. The next day serum from the mice was diluted and added to the wells. After 1 hour the plates were rinsed with PBS and rabbit anti-mouse IgG coupled to peroxidase was added to the wells. The plates were incubated for 30 min and then the resulting UV absorbance was measured using a micro-titer plate reader. The titer was defined as the highest dilution of the serum which resulted in a two-fold increase from background absorbance (approximately 0.50 OD).

The results are shown in FIG. 6. The open circles represent the data obtained from animals injected with native ADI, which was very antigenic. The filled circles represent the data obtained from the animals injected with ADI-SS-PEG5,000, while the open triangles represent the data obtained from the animals injected with ADI-SS-PEG20,000. As can be seen from FIG. 6, ADI-SS-PEG5,000 and ADI-SS-PEG20,000 are significantly less antigenic than native ADI. For example, as few as 4 injections of native ADI resulted in a titer of about $10^6$, while 4 injections of any of the PEG-ADI formulations failed to produce any measurable antibody. However, after 8 injections, the ADI-PEG5,000 had a titer of about $10^2$, while ADI-PEG20,000 did not induce this much of an immune response until after 12 injections. The results demonstrate that attaching PEG to ADI blunts the immune response to the protein.

Example 7

Tumor Inhibition of Human Melanomas

Figure 7:
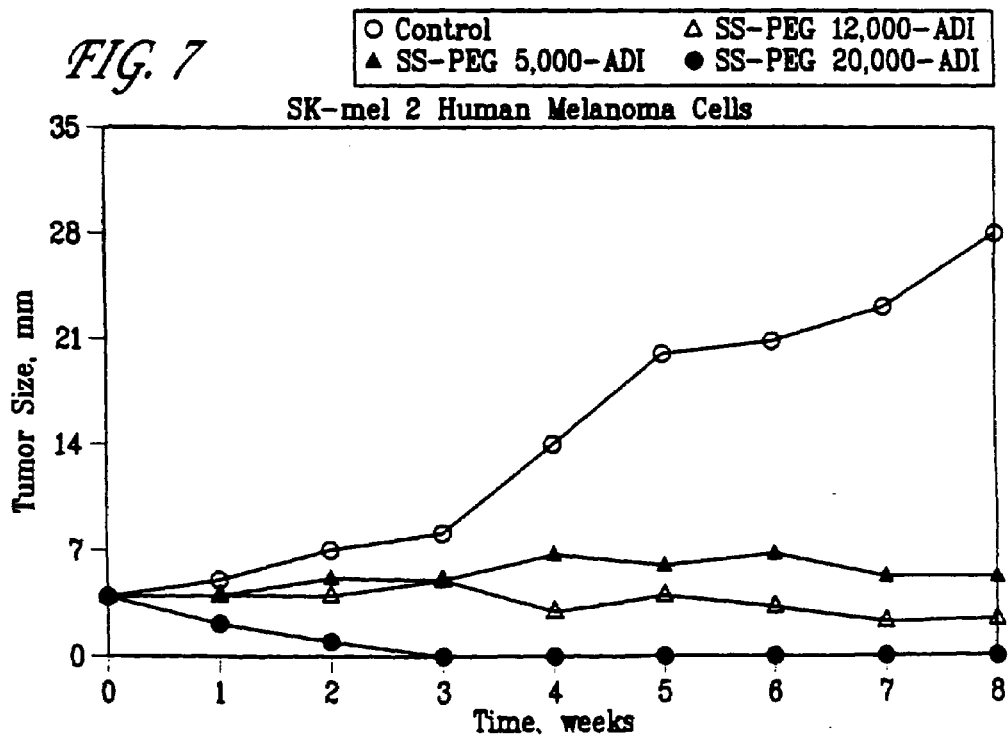
FIG. 7 is a graph showing the effect that treatments with ADI-SS-PEG5,000, ADI-SS-PEG12,000 or ADI-SS-PEG20,000 had on tumor size in mice which were injected with SK-mel 2 human melanoma cells.

The effect of PEG-ADI on the growth of human melanoma (SK-Mel 28) in nude mice was determined. Nude mice (5 in each group) were injected with $10^6$ SK-mel 2 human melanoma cells which were allowed to grow until the tumors reached a diameter of about 3-5 mm. The mice were left untreated (open circles) or were treated once a week for 8 weeks with 5.0 IU of ADI-SS-PEG5,000 (filled triangles), ADI-SS-PEG12,000 (open triangles) or ADI-SS-PEG20,000 (filled circles). The tumor size was measured weekly, and the mean diameter of the tumors is presented in FIG. 7.

Figure 8:
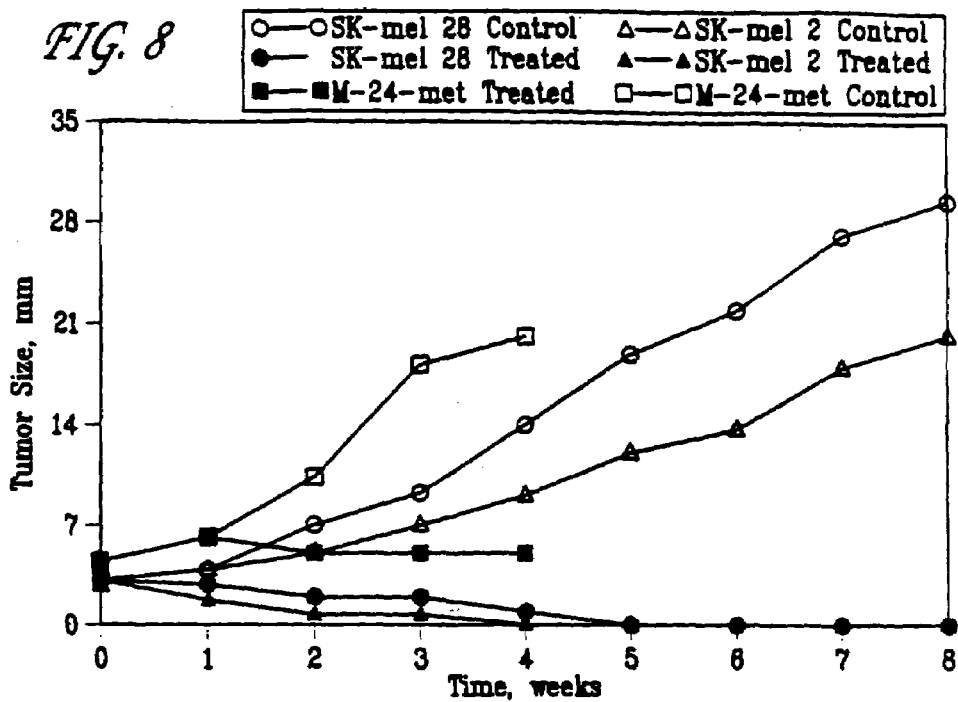
FIG. 8 is a graph showing the effect that treatments with ADI-PEG20,000 had on tumor size in mice which were injected with SK-mel 28, SK-mel 2 or M24-met human melanoma cells.

FIG. 8 shows the effectiveness of ADI-SS-PEG20,000 on three human melanomas (SK-mel 2, SK-mel 28, M24-met) grown in vivo in nude mice. Nude mice (5 in each group) were injected with $10^6$ SK-mel 2, SK-mel 28 or M24-met human melanoma cells. The tumors were allowed to grow until they were approximately 3-5 mm in diameter. Thereafter, the animals were injected once a week with 5.0 IU of ADI-SS-PEG20,000. The results are shown in FIG. 8, and show that PEG-ADI inhibited tumor growth and that eventually the tumors began to regress and disappear. Because the tumors did not have argininosuccinate synthatase, they were unable to synthesize proteins (because ADI eliminated arginine and the tumors could not make it) so that the cells "starved to death."

Since M24-met human melanoma is highly metastatic, the animals injected with M24-met human melanoma cells were sacrificed after 4 weeks of treatment and the number of metastases in the lungs of the animals was determined. The control animals had an average of 32 metastases, while the animals treated with ADI-SS-PEG20,000 did not have any metastases. The results appear to indicate that ADI-SS-PEG20,000 not only inhibited the growth of the primary melanoma tumor, but also inhibited the formation of metastases.

It is of interest to note that in over 200 animals tested, the average number of metastases in the control group was 49±18, while only a single metastasis was observed in 1 treated animal.

Example 8

Tumor Inhibition of Human Hepatomas

Figure 9:
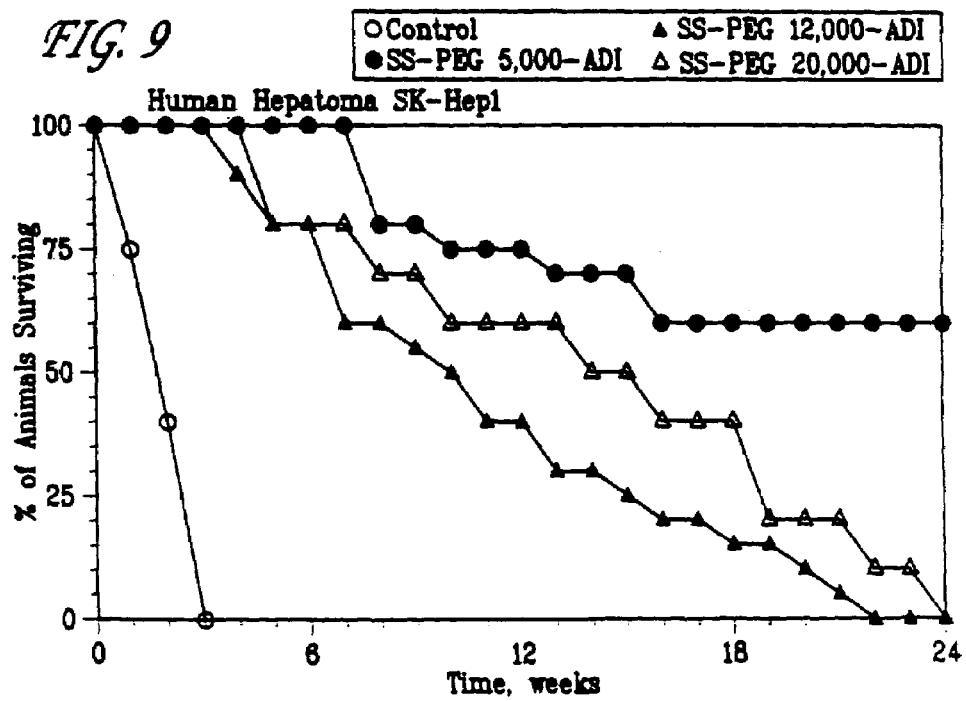
FIG. 9 is a graph showing the effect that treatments with ADI-PEG5,000, ADI-PEG12,000 or ADI-PEG20,000 had on the survival of mice which were injected with human hepatoma SK-Hep1 cells.

The ability of PEG-ADI to inhibit the growth of a human hepatoma in vivo was tested. Nude mice (5 in each group) were injected with $10^6$ human hepatoma SK-Hep1 cells. The tumors were allowed to grow for two weeks and then the animals were treated once a week with 5.0 IU of SS-PEG5,000-ADI (solid circles), SS-PEG12,000-ADI (solid triangles) or SS-PEG20,000-ADI (open triangles). The results are set forth in FIG. 9. The untreated animals (open circles) all died within 3 weeks. In contrast, animals treated with ADI had a far longer life expectancy, as can be seen from FIG. 9. All the surviving mice were euthanized after 6 months, and necropsy indicated that they were free of tumors.

Surprisingly, PEG5,000-ADI is most effective in inhibiting hepatoma growth in vivo. The exact mechanism by which this occurs is unknown. Without being bound to any theory of the invention works, it appears that proteins formulated with SS-PEG5,000-ADI become sequestered in the liver. Larger molecular weights of PEG do not, which may be due to the uniqueness of the hepatic endothelium and the spaces (fenestrae) being of such a size that larger molecular weights of PEG-ADI conjugates are excluded.

Example 9

Application to Humans

PEG5,000-ADI and PEG20,000-ADI were incubated ex vivo with normal human serum and the effects on arginine concentration was determined by amino acid analysis, where the enzyme was found to be fully active and capable of degrading all the detectable arginine with the same kinetics as in the experiments involving mice. The reaction was conducted at a volume of 0.1 ml in a time of 1 hour at 37° C. Additionally, the levels of arginine and citrulline in human serum are identical with that found in mice. PEG-proteins circulate longer in humans than they do in mice. For example, the circulating half life of PEG conjugated adenosine deiminase, asparaginase, glucocerbrocidase, uricase, hemoglobulin and superoxide dismutase all have a circulating half life that is 5 to 10 times longer than the same formulations in mice. What this has meant in the past is that the human dose is most often 1/5 to 1/10 of that used in mice. Accordingly, PEG-ADI should circulate even longer in humans than it does in mice.

Each of the patents, patent applications and publications described herein are hereby incorporated by reference herein in their entirety.

Various modifications of the invention, in addition to those described herein, will be apparent to one skilled in the art in view of the foregoing description. Such modifications are also intended to fall within the scope of the appended claims.

What is claimed is:

1. A method of enhancing the circulating half life of arginine deiminase comprising modifying said arginine deiminase by covalently bonding said arginine deiminase via a linking group to polyethylene glycol, wherein the arginine deiminase is derived from a microorganism of the genus selected from the group consisting of: *Steptococcus, Borrelia, Qiardia, Clostridium, Enterococcus, Lactobacillus*, and *Bacillus;* wherein the polyethylene glycol has a total weight average molecular weight of from about 1,000 to about 40,000, and wherein the linking group is selected from the group consisting of a succinimide group, an amide group, an imide group, a carbamate group, an ester group, an epoxy group, a carboxyl group, a hydroxyl group, a carbohydrate, a tyrosine group, a cysteine group, a histidine group and combinations thereof.

2. A method of treating a tumor in a patient comprising administering to said patient a compound comprising arginine deiminase covalently bonded via a linking group to polyethylene glycol, wherein the arginine deiminase is derived from a microorganism of the genus selected from the group consisting of: *Steptococcus, Borrelia, Qiardia, Clostridium, Enterococcus, Lactobacillus*, and *Bacillus;* wherein the polyethylene glycol has a total weight average molecular weight of from about 1,000 to about 40,000, and wherein the linking group is selected from the group consisting of a succinimide group, an amide group, an imide group, a carbamate group, an ester group, an epoxy group, a carboxyl group, a hydroxyl group, a carbohydrate, a tyrosine group, a cysteine group, a histidine group and combinations thereof.

3. The method of claim 2, wherein said tumor is a melanoma.

4. The method of claim 3, wherein said polyethylene glycol has a total weight average molecular weight of about 20,000.

5. The method of claim 3, wherein said linking group is a succinimide group.

6. The method of claim 5, wherein said succinimide group is succinimidyl succinate, succinimidyl propionate, succinimidyl carboxymethylate, succinimidyl succinamide, N-hydroxy succinimide or combinations thereof.

7. The method of claim 2, wherein said tumor is a hepatoma.

8. The method of claim 7, wherein said polyethylene glycol has a total weight average molecular weight of about 20,000.

9. The method of claim 7, wherein said linking group is a succinimide group.

10. The method of claim 9, wherein said succinimide group is succinimidyl succinate, succinimidyl propionate, succinimidyl carboxymethylate, succinimidyl succinamide, N-hydroxy succinimide or combinations thereof.

11. The method of claim 2, wherein said tumor is a sarcoma.

* * * * *